US012111313B2

(12) United States Patent
Kornberg

(10) Patent No.: US 12,111,313 B2
(45) Date of Patent: Oct. 8, 2024

(54) CHELATOR-COATED FIELD EFFECT TRANSISTOR AND DEVICES AND METHODS USING SAME

(71) Applicant: SENSOR-KINESIS CORPORATION, Los Angeles, CA (US)

(72) Inventor: Roger D. Kornberg, Atherton, CA (US)

(73) Assignee: Autonomous Medical Devices Inc., Santa Ana, CA (US)

( * ) Notice: Subject to any disclaimer, the term of this patent is extended or adjusted under 35 U.S.C. 154(b) by 675 days.

(21) Appl. No.: 17/264,281

(22) PCT Filed: Aug. 14, 2019

(86) PCT No.: PCT/US2019/046568
§ 371 (c)(1),
(2) Date: Jan. 28, 2021

(87) PCT Pub. No.: WO2020/037078
PCT Pub. Date: Feb. 20, 2020

(65) Prior Publication Data
US 2021/0293798 A1 Sep. 23, 2021

Related U.S. Application Data

(60) Provisional application No. 62/718,632, filed on Aug. 14, 2018.

(51) Int. Cl.
*G01N 33/543* (2006.01)
*G01N 27/414* (2006.01)

(52) U.S. Cl.
CPC ... *G01N 33/54373* (2013.01); *G01N 27/4145* (2013.01); *G01N 27/4146* (2013.01); *G01N 33/5432* (2013.01)

(58) Field of Classification Search
USPC ....... 422/82.01; 436/524, 525, 806; 438/142
See application file for complete search history.

(56) References Cited

U.S. PATENT DOCUMENTS

| | | | |
|---|---|---|---|
| 6,485,983 B1 * | 11/2002 | Lu | G01N 33/558 436/514 |
| 2009/0026082 A1 | 1/2009 | Rothberg | |
| 2009/0127589 A1 | 5/2009 | Rothberg | |
| 2010/0137143 A1 | 6/2010 | Rothberg | |
| 2010/0197507 A1 | 8/2010 | Rothberg | |
| 2010/0285601 A1 | 11/2010 | Kong | |
| 2010/0300559 A1 | 12/2010 | Schultz | |
| 2010/0300895 A1 | 12/2010 | Nobile | |
| 2010/0301398 A1 | 12/2010 | Rothberg | |
| 2011/0159481 A1 | 6/2011 | Liu | |
| 2017/0131267 A1 * | 5/2017 | Lee | H01L 29/205 |

FOREIGN PATENT DOCUMENTS

WO WO-2017196676 A1 * 11/2017

* cited by examiner

*Primary Examiner* — Christopher L Chin
(74) *Attorney, Agent, or Firm* — Marcus C. Dawes

(57) ABSTRACT

A field effect transistor comprising a chelator or derivatized chelator, a device for detecting a marker in a sample comprising said sensor, a method for detecting metal ions in a sample comprising said sensor or device and a sensor and method for detecting a marker in a sample.

22 Claims, 13 Drawing Sheets

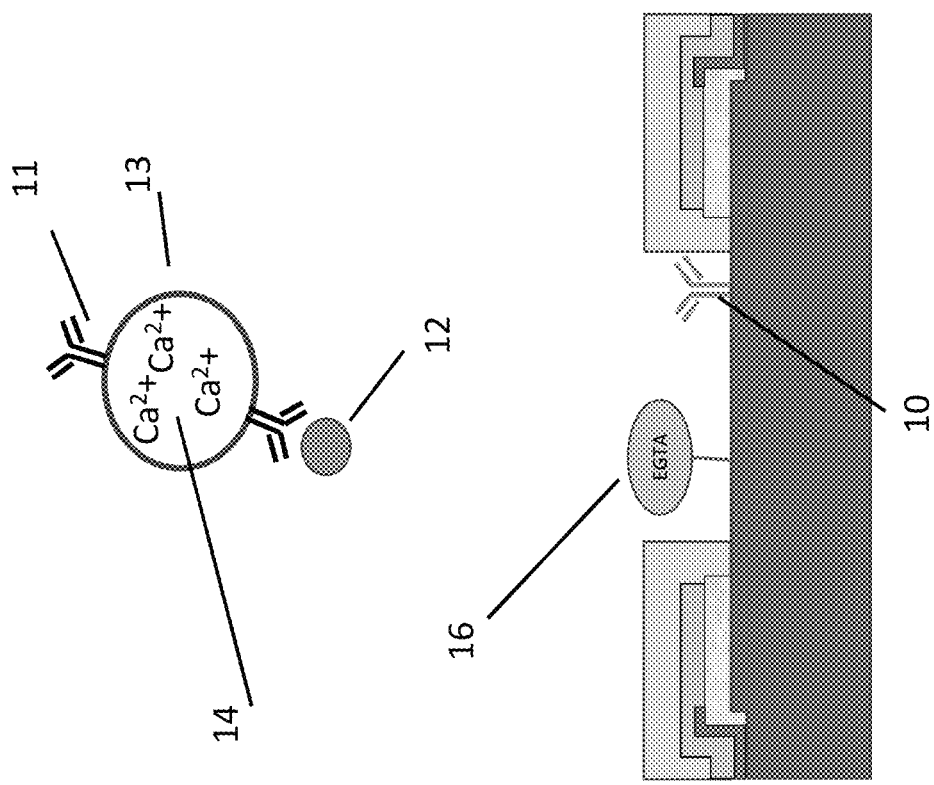

CHELATOR-COATED FIELD EFFECT TRANSISTOR AND DEVICES AND METHODS USING SAME

CROSS-REFERENCE TO RELATED APPLICATIONS

This application claims priority from U.S. Provisional Application No. 62/718,632, filed Aug. 14, 2018, the contents of which are hereby incorporated by reference in their entirety.

BACKGROUND OF THE DISCLOSURE

There is a need for convenient and portable methods and devices for the detection of markers, including biomarkers and environmental markers, especially more sensitive, specific, and robust sensors. See, e.g., Kaisti, M. *Biosensors and Bioelectronics,* 2017, vol. 98:437-448, incorporated by reference herein in its entirety. By contrasts, interactions involving macromolecules, such as antibodies, occur relatively slowly, on the order of $10^5$ specific binding events per second.

Binding of ions to counter ions occurs much more rapidly, on the order of $10^{10}$ or more events per second. The detection of ions in solution, however, is complicated by the screening of detectors from such molecules by oppositely charged ions and other unrelated ions in the solution. See, e.g., Kaisti, M. *Biosensors and Bioelectronics,* 2017, vol. 98:437-448, incorporated by reference herein in its entirety. Accordingly, there is a need in the art for improving the selective, sensitive and robust detection of ions in a solution.

Among various potentiometric techniques, detection based on field-effect transistors (FETs) has attracted considerable attention because of its potential for miniaturization, parallel sensing, fast response time, and seamless integration with electronic manufacturing processes.

Silicon-based FET devices have been successful and have seen continual improvements in key parameters such as on-resistance RDS(on), voltage ratings, switching speed, packaging, and other attributes. However, the rate of improvements in these FETs has leveled off, as their performance is now close to the theoretical limit as determined by the underlying fundamental physics of these materials and processes. Gallium nitride (GaN) is a semiconductor that possesses unique characteristics that make it advantageous for the creation of efficient optoelectronic devices in addition to high power and high-temperature applications.

SUMMARY OF THE DISCLOSURE

In some embodiments, the present disclosure provides a field effect transistor (FET) comprising a chelator or a derivative of a chelator. In other embodiments, the present disclosure provides devices comprising such FETs and methods of using such FETs and devices.

A first aspect of the present disclosure provides a field-effect transistor. In some embodiments, the field-effect transistor comprises: (a) a source, (b) a drain, (c) a gate, (d) a substrate at least partially interposed between the source and the gate, and at least partially interposed between the drain and the gate; and (e) a chelator or a derivatized chelator at least partially interposed between the source and the drain.

A second aspect of the present disclosure provides a device for sample testing. In some embodiments, the device comprises: (1) a field-effect transistor comprising: (a) a source, (b) a drain, (c) a gate, (d) a substrate at least partially interposed between the source and the gate, and at least partially interposed between the drain and the gate; and (e) a chelator or a derivatized chelator at least partially interposed between the source and the drain; and (2) a communication port configured to transmit sensor data based on a signal provided via at least one of the source or the drain.

A third aspect of the present disclosure provides a method for detecting a metal ion, identifying a metal ion, or measuring an aspect of the metal ion. In some embodiments, the method uses a field-effect transistor or a device as described in the present disclosure, the method comprising: (1) contacting the field-effect transistor with a detectable label comprising a metal ion, thereby placing the detectable label in contact with the chelator or the derivatized chelator; (2) selectively binding the metal ion to the chelator or the derivatized chelator thereby causing a change in an electrical current between the source and the drain; and (3) generating an output representing the change in the electrical current for use in at least one of detecting the metal ion, identifying the metal ion, or measuring an aspect of the metal ion.

A fourth aspect of the present disclosure provides a sensor for the detection of markers in combination with a liposome in solution containing a metal ion, the liposome including a detection antibody configured to bind a target marker. In some embodiments, the sensor comprises:
  (a) a field-effect transistor with a source-drain channel functionalized with a capture antibody to selectively bind to the target marker; and
  (b) a metal ion chelator or metal ion derivatized chelator in the source-drain channel, which metal ion chelator or metal ion derivatized chelator selectively binds with the metal ion in the liposome to cause a change in current in the field-effect transistor.

A fifth aspect of the present disclosure provides a method for the detection of a marker. In some embodiments, the method comprises:
  (a) providing a liposome in solution containing a metal ion, the liposome including a detection antibody configured to bind a target marker; and
  (b) providing a field-effect transistor with a source-drain channel functionalized with a capture antibody to selectively bind to the target marker;
  (c) providing a metal ion chelator or metal ion derivatized chelator in the source-drain channel;
  (d) selectively binding the metal ion chelator or metal ion derivatized chelator with the metal ion in the liposome; and
  (e) causing a change in current in the field-effect transistor as a result of the selective binding the metal ion chelator or metal ion derivatized chelator with the metal ion in the liposome; and
  wherein the detection of the metal ions is indicative of detection of the marker.

In a sixth aspect, the present disclosure provides an improved selective, sensitive and robust method for the detection of a marker. In some embodiments, the method uses a chelator-coated field effect transistor defined on a transistor substrate and having a source-drain channel functionalized with a capture antibody to selectively bind to the marker, the field effect transistor characterized by a conductivity and gain (beta). Optionally, the method comprises:
  disposing a metal ion chelator or metal ion derivatized chelator in the source-drain channel;
  disposing a liposome containing a metal ion into the source-drain channel of the field effect transistor, the liposome including a detection antibody configured to selectively bind the marker;

disrupting the liposome to release at least some of the metal ion within the liposome into the source-drain channel of the field effect transistor;

selectively conjugating the metal ion chelator or metal ion derivatized chelator with the metal ion in the liposome to immobilize the marker on the transistor substrate; and washing the source-drain channel of the field effect transistor;

detecting an amplified detectable current in the field-effect transistor as a result of the selective conjugation of the metal ion chelator or metal ion derivatized chelator with the metal ion in the liposome by changing the conductivity of the field effect transistor and thereby changing the gain (beta) of the field effect transistor, whereby detection of metal ions indicative of detection of the marker is achieved. Optionally, the limit of detection is improved.

In any of the FETs, sensors, devices, or methods disclosed herein, the metal ion being detected is, optionally, selected from the group consisting of $Ca^{2+}$, $Fe^{2+}$, $Fe^{3+}$, $Mg^{2+}$, $Mn^{2+}$, $Cu^{2+}$, $Cu^{3+}$, $Zn^{2+}$, $Ni^{2+}$, $Co^{2+}$ and a heavy metal ion (e.g., $As^{+3}$, $Hg^{+2}$, $Sb^{+3}$, and $Au^{+}$).

In any of the FETs, sensors, devices, or methods disclosed herein, the chelator is, optionally, selected from the group consisting of a $Ca^{2+}$ chelator, a $Fe^{2+}$ chelator, a $Fe^{3+}$ chelator, a $Mg^{2+}$ chelator, a $Mn^{2+}$ chelator, a $Cu^{2+}$ chelator, a $Cu^{3+}$ chelator, a $Zn^{2+}$ chelator, a $Ni^{2+}$ chelator, a $Co^{2+}$ chelator and a heavy metal ion chelator (e.g., an $As^{+3}$ chelator, a $Hg^{+2}$ chelator, a $Sb^{3+}$ chelator, and an $Au^{+}$ chelator).

Particular embodiments of the disclosure are set forth in the following numbered paragraphs:

1. A field-effect transistor comprising:
   (a) a source,
   (b) a drain,
   (c) a gate,
   (d) a substrate at least partially interposed between the source and the gate, and at least partially interposed between the drain and the gate; and
   (e) a chelator or a derivatized chelator at least partially interposed between the source and the drain.
2. The field-effect transistor of paragraph 1, wherein the substrate comprises Gallium Nitride.
3. The field-effect transistor of paragraph 1 or 2, wherein the substrate comprises a dielectric material.
4. The field-effect transistor of any one of paragraphs 1-3, wherein the chelator or the derivatized chelator is at least partially interposed upon the substrate.
5. The field-effect transistor of any one of paragraphs 1-4, wherein the chelator or the derivatized chelator is at least partially interposed upon the substrate and is at least partially interposed between the source and the drain.
6. The field-effect transistor of any one of paragraphs 1-5, wherein the source and/or drain and/or gate comprises a material selected from the group of chromium, titanium, copper, aluminum, molybdenum, tungsten, nickel, gold, palladium, platinum, conducting polymers and oligomers, silver paste and a combination thereof.
7. The field-effect transistor of paragraph 6, wherein the source and/or drain and/or gate comprises a combination of titanium and platinum or a combination of titanium and gold.
8. The field-effect transistor of any one of paragraphs 1-7, wherein the field-effect transistor further comprises a carbon nanotube.
9. The field-effect transistor of paragraph 8, wherein the carbon nanotube is at least partially interposed upon the substrate.
10. The field-effect transistor of paragraph 8 or 9, wherein the carbon nanotube is at least partially interposed between the source and the drain.
11. The field-effect transistor of any one of paragraphs 8-10, wherein the carbon nanotube is at least partially interposed upon the dielectric material and is at least partially interposed between the source and the drain.
12. The field-effect transistor of any one of paragraphs 8-11, wherein the chelator or the derivatized chelator is at least partially interposed upon the carbon nanotube.
13. The field-effect transistor of any one of paragraphs 8-12, wherein the chelator or the derivatized chelator is at least partially interposed upon the substrate.
14. The field-effect transistor of any one of paragraphs 8-13, wherein the chelator or the derivatized chelator is at least partially interposed upon the substrate and is at least partially interposed between the source and the drain.
15. The field-effect transistor of any one of paragraphs 1-14, wherein the chelator or the derivatized chelator is configured to contact a detectable label.
16. The field-effect transistor of paragraphs 15, wherein the detectable label comprises a metal ion.
17. The field-effect transistor of paragraph 16, wherein the metal ion is selected from the group consisting of $Ca^{2+}$, $Fe^{2+}$, $Fe^{3+}$, $Mg^{2+}$, $Mn^{2+}$, $Cu^{2+}$, $Cu^{3+}$, $Zn^{2+}$, $Ni^{2+}$, $Co^{2+}$ and a heavy metal ion.
18. The field-effect transistor of paragraph 16, wherein the chelator or the derivatized chelator is configured to selectively bind the metal ion, and the binding between the chelator or the derivatized chelator and the metal ion causes a change in an electrical current between the source and the drain.
19. The field-effect transistor of paragraph 18, wherein the change in the electrical current is provided as output for use in at least one of detecting the metal ion, identifying the metal ion, or measuring an aspect of the metal ion.
20. The field-effect transistor of paragraph 18, wherein a first electrical voltage is applied to the source and a second electrical voltage is applied to the drain, the first electrical voltage being different from the second electrical voltage, thereby contributing to the electrical current between the source and the drain.
21. The field-effect transistor of any one of paragraphs 16-20, wherein the metal ion is $Ca^{2+}$.
22. The field-effect transistor of paragraph 21, wherein the chelator or the derivatized chelator is selected from the group consisting of ethylene glycol-bis(β-aminoethyl ether)-N,N,N',N'-tetraacetic acid (EGTA); ethylene diamine tetra acetic acid (EDTA); N-(2-Hydroxyethyl) ethylenediamine-N, N', N'-triacetic acid Trisodium salt (HEDTA); Nitrilotriacetic acid (NTA); BAPTA; 5,5'-dimethyl BAPTA (tetrapotassium salt); DMNP-EDTA; INDO 1 pentapotassium salt; FURA-2 pentapotassium salt; FURA 2/AM; MAPTAM; FLUO 3 (pentaammonium salt); Tetraacetoxymethyl Bis(2-aminoethyl) Ether N,N,Nprime,Nprime-Tetraacetic Acid; and derivatives thereof.
23. The field-effect transistor of paragraph 22, wherein the chelator or the derivatized chelator is EGTA or a derivative thereof.
24. The field-effect transistor of any one of paragraphs 16-20, wherein the metal ion is $Fe^{2+}$ or $Fe^{3+}$.

25. The field-effect transistor of paragraph 24, wherein the chelator or derivatized chelator is selected from the group consisting of deferasirox; deferiprone; deferoxamine; desferrioxamine; desferrithiocin[2-(3-hydroxypyridin-2-yl)-4-methyl-4,5-dihyrothiazole-4-carboxylic acid; clioquinol; O-trensox (Tris-N-(2-aminoethyl-[8-hydroxyquinoline-5-sulfonato-7-carboxamido]amine); tachpyr (N,N',N"-tris(2-pyridylmethyl)-cis,cis-1,3,5-triamino-cyclohexane); dexrazoxane; triapine (3-aminopyridine-2-carboxaldehyde thiosemicarbazone); pyridoxal isonicotinoyl hydrazone; di-2-pyridylketone thiosemicarbazone series; flavan-3-ol; curcumin; apocynin; kolaviron; floranol; baicalein; baicalin; *Ligusticum wallichi* Francha (ligustrazine); quercetin; epigallocatechin gallate; theaflavin; phytic acid; genistein (5,7,4'-tri-hydroxyisoflavone); EDTA; NTA; HBED, o-Phenanthroline monohydrate; Pyridoxal Isonicotinoyl Hydrazone, 2,2prime-Dipyridyl, (S)-1-(p-Bromoacetamidobenzyl)ethylenediaminetetraacetic Acid, (S)-1-(4-Aminoxyacetamidobenzyl)ethylenediaminetetraacetic Acid; and derivatives thereof.
26. The field-effect transistor of any one of paragraphs 16-20, wherein the metal ion is $Mg^{2+}$.
27. The field-effect transistor of paragraph 26, wherein the chelator or the derivatized chelator is selected from the group consisting of EDTA, EGTA, HEDTA, NTA and derivatives thereof.
28. The field-effect transistor of any one of paragraphs 16-20, wherein the metal ion is $Mn^{2+}$.
29. The field-effect transistor of paragraph 28, wherein the chelator or the derivatized chelator is selected from the group consisting of EDTA; EGTA; HEDTA; NTA; triethylenetetramine-N,N,N',N",N''',N'''-hexaacetic acid (TTHA); diethylenetriaminepentaacetic acid (DTPA); DPTA; DPTA-OH; HBED; and derivatives thereof.
30. The field-effect transistor of any one of paragraphs 16-20, wherein the metal ion is $Cu^{2+}$ or $Cu^{3+}$.
31. The field-effect transistor of paragraph 30, wherein the chelator or the derivatized chelator is selected from the group consisting of EDTA; NTA; D-Penicillamine (DPA); Tetraethylenetetraamine (TETA); clioquinol and derivatives thereof.
32. The field-effect transistor of any one of paragraphs 16-20, wherein the metal ion is $Zn^{2+}$.
33. The field-effect transistor of paragraph 32, wherein the chelator or the derivatized chelator is selected from the group consisting of ADAMTS-5 Inhibitor; N,N,N',N'-tetrakis(2-pyridinylmethyl)-1,2-ethanediamine (TPEN); EDPA; 1,2-bis(o-aminophenoxy)ethane-N,N,N',N'-tetraacetic acid (BAPTA); CaEDTA; EDTA; EGTA; Tricine; ZX1; 4-{[2-(bis-pyridin-2-ylmethylamino)ethylamino]methyl}phenyl)methanesulfonic acid (DPESA); [4-({[2-(bis-pyridin-2-ylmethylamino)ethyl]pyridin-2-ylmethylamino}-methyl)phenyl]methanesulfonic acid (TPESA); and derivatives thereof.
34. The field-effect transistor of any one of paragraphs 16-20, wherein the metal ion is $K^+$.
35. The field-effect transistor of paragraph 34, wherein the chelator or the derivatized chelator is selected from the group consisting of calcium polystyrene sulfonate; sodium polystyrene sulfonate; patiromer; sodium zirconium cyclosilicilate; D-tartrate monobasic; and derivatives thereof.
36. The field-effect transistor of any one of paragraphs 16-20, wherein the metal ion is a heavy metal ion.
37. The field-effect transistor of paragraph 36, wherein the heavy metal ion is selected from the group consisting of $As^{+3}$, $Hg^{+2}$, $Sb^{+3}$, and $Au^+$.
38. The field-effect transistor of paragraph 36 or 37, wherein the chelator or the derivatized chelator is selected from the group consisting of Dimercaprol (2,3-dimercapto-1-propanol); Sodium 2,3-dimercaptopropanesulfonate monohydrate; 2,3-Dimercapto-1-propanesulfonic acid sodium salt; and derivatives thereof.
39. The field-effect transistor of any of paragraphs 1-38, further comprising an antibody or a derivatized antibody.
40. The field-effect transistor of paragraph 39, wherein the antibody or derivatized antibody is at least partially interposed upon the substrate.
41. The field-effect transistor of paragraph 39 or 40, wherein the antibody or derivatized antibody is configured to immobilize a marker.
42. A device comprising the field-effect transistor of any of paragraphs 1-41 and a communication port configured to transmit data based on a signal provided via at least one of the source or the drain.
43. The device of paragraph 42, further comprising:
    a signal processor,
    wherein the signal processor is coupled to the communication module and is coupled to at least one of the source or the drain, and
    wherein the signal processor is configured to subject the signal to one or more signal processing algorithms, including at least one of an algorithm for detecting the metal ion, an algorithm for identifying the metal ion, or an algorithm measuring an aspect of the metal ion.
44. The device of paragraph 43, wherein the signal processor generates an output based on the one or more signal processing algorithms and provides the output as the data via the communication port.
45. The device of any one of paragraphs 42-44, wherein the metal ion is $Ca^{2+}$.
46. The device of any one of paragraphs 42-45, wherein the device is a microfluidics device.
47. The device of any one of paragraphs 42-46, further comprising means for receiving a sample, wherein the sample comprises a marker.
48. The device of paragraph 47, wherein the marker is a biomarker, an environmental marker, an allergen, or a microorganism.
49. The device of paragraph 47, wherein the sample is an environmental sample, a food sample, or a sample obtained from a subject.
50. The device of paragraph any one of paragraphs 47-49, wherein the field-effect transistor comprises an antibody or a derivatized antibody that binds the marker.
51. The device of paragraph 50, wherein the device further comprises means for washing the antibody-bound marker.
52. A method for detecting metal ions, identifying metal ions or measuring an aspect of metal ions through the use of a field-effect transistor according to any one of paragraphs 1-41 or the device according to any one of paragraphs 42-51, the method comprising:
    (a) contacting the field-effect transistor with a detectable label comprising a metal ion, thereby placing the detectable label in contact with the chelator or the derivatized chelator;

(b) selectively binding the metal ion to the chelator or the derivatized chelator thereby causing a change in an electrical current between the source and the drain; and
(c) generating an output representing the change in the electrical current for use in at least one of detecting the metal ion, identifying the metal ion, or measuring an aspect of the metal ion.

53. A sensor for the detection of markers in combination with a liposome in solution containing a metal ion, the liposome including an antibody configured to bind a target marker; the sensor comprising:
(a) a field-effect transistor with a source-drain channel functionalized with a capture antibody to selectively bind to the target marker; and
(b) a metal ion chelator or metal ion derivatized chelator in the source-drain channel, which metal ion chelator or metal ion derivatized chelator selectively binds with the metal ion in the liposome to cause a change in current in the field-effect transistor.

54. The sensor according to paragraph 53, whereby binding of metal ions occurs on the order of $10^8$-$10^{12}$ events per second without substantial interference of the detection of the metal ions by screening by oppositely charged ions and unrelated ions in the solution.

55. The sensor according to paragraph 54, whereby binding of metal ions occurs on the order of $10^{10}$ or more events per second without substantial interference of the detection of the metal ions by screening by oppositely charged ions and unrelated ions in the solution for improved selective, sensitive and robust detection of metal ions indicative of detection of the target marker.

56. The sensor according to any one of paragraphs 53-55, wherein the source-drain channel of the field-effect transistor comprises Gallium Nitride.

57. The sensor according to any one of paragraphs 53-56, wherein the source and/or the drain comprises a material selected from the group of chromium, titanium, copper, aluminum, molybdenum, tungsten, nickel, gold, palladium, platinum, conducting polymers and oligomers, silver paste and combination thereof 58. The sensor according to any one of paragraphs 53-56, wherein the source and/or the drain comprises a combination of titanium and platinum or a combination of titanium and gold.

59. The sensor according to any one of paragraphs 53-58, wherein the field-effect transistor further comprises a carbon nanotube.

60. The sensor according to paragraph 59, wherein the carbon nanotube is at least partially interposed between the source and the drain.

61. The sensor according to paragraph 59 or 60, wherein the chelator or the derivatized chelator is at least partially interposed upon the carbon nanotube.

62. The sensor according to any one of paragraphs 53-61, wherein the metal ion is selected from the group consisting of $Ca^{2+}$, $Fe^{2+}$, $Fe^{3+}$, $Mg^{2+}$, $Mn^{2+}$, $Cu^{2+}$, $Cu^{3+}$, $Zn^{2+}$, $Ni^{2+}$, $Co^{2+}$ and a heavy metal ion.

63. The sensor according to any one of paragraphs 53-61, wherein the metal ion is $Ca^{2+}$.

64. The sensor according to paragraph 63, wherein the chelator or the derivatized chelator is selected from the group consisting of ethylene glycol-bis(3-aminoethyl ether)-N,N,N',N'-tetraacetic acid (EGTA); ethylene diamine tetra acetic acid (EDTA); N-(2-Hydroxyethyl) ethylenediamine-N, N', N'-triacetic acid Trisodium salt (HEDTA); Nitrilotriacetic acid (NTA); BAPTA; 5,5'-dimethyl BAPTA (tetrapotassium salt); DMNP-EDTA; INDO 1 pentapotassium salt; FURA-2 pentapotassium salt; FURA 2/AM; MAPTAM; FLUO 3 (pentaammonium salt); Tetraacetoxymethyl Bis(2-aminoethyl) Ether N,N,Nprime,Nprime-Tetraacetic Acid; and derivatives thereof.

65. The sensor according to paragraph 63, wherein the chelator or the derivatized chelator is EGTA or a derivative thereof.

66. The sensor according to any one of paragraphs 53-61, wherein the metal ion is $Fe^{2+}$ or $Fe^{3+}$.

67. The sensor according to paragraph 66, wherein the chelator or derivatized chelator is selected from the group consisting of deferasirox; deferiprone; deferoxamine; desferrioxamine; desferrithiocin[2-(3-hydroxypyridin-2-yl)-4-methyl-4,5-dihyrothiazole-4-carboxylic acid; clioquinol; O-trensox (Tris-N-(2-aminoethyl-[8-hydroxyquinoline-5-sulfonato-7-carboxamido] amine); tachpyr (N,N',N''-tris(2-pyridylmethyl)-cis,cis-1,3,5-triamino-cyclohexane); dexrazoxane; triapine (3-aminopyridine-2-carboxaldehyde thiosemicarbazone); pyridoxal isonicotinoyl hydrazone; di-2-pyridylketone thiosemicarbazone series; flavan-3-ol; curcumin; apocynin; kolaviron; floranol; baicalein; baicalin; *Ligusticum wallichi* Francha (ligustrazine); quercetin; epigallocatechin gallate; theaflavin; phytic acid; genistein (5,7,4'-tri-hydroxyisoflavone); EDTA; NTA; HBED, o-Phenanthroline monohydrate; Pyridoxal Isonicotinoyl Hydrazone, 2,2prime-Dipyridyl, (S)-1-(p-Bromoacetamidobenzyl)ethylenediaminetetraacetic Acid, (S)-1-(4-Aminoxyacetamidobenzyl)ethylenediaminetetraacetic Acid; and derivatives thereof.

68. The sensor according to any one of paragraphs 53-61, wherein the metal ion is $Mg^{2+}$.

69. The sensor according to paragraph 68, wherein the chelator or the derivatized chelator is selected from the group consisting of EDTA, EGTA, HEDTA, NTA and derivatives thereof.

70. The sensor according to any one of paragraphs 53-61, wherein the metal ion is $Mn^{2+}$.

71. The sensor according to paragraph 70, wherein the chelator or the derivatized chelator is selected from the group consisting of EDTA; EGTA; HEDTA; NTA; triethylenetetramine-N,N,N',N'',N''',N'''-hexaacetic acid (TTHA); diethylenetriaminepentaacetic acid (DTPA); DPTA; DPTA-OH; HBED; and derivatives thereof.

72. The sensor according to any one of paragraphs 53-61, wherein the metal ion is $Cu^{2+}$ or $Cu^{3+}$.

73. The sensor according to paragraph 72, wherein the chelator or the derivatized chelator is selected from the group consisting of EDTA; NTA; D-Penicillamine (DPA); Tetraethylenetetraamine (TETA); clioquinol and derivatives thereof.

74. The sensor according to any one of paragraphs 53-61, wherein the metal ion is $Zn^{2+}$.

75. The sensor according to paragraph 74, wherein the chelator or the derivatized chelator is selected from the group consisting of ADAMTS-5 Inhibitor; N,N,N',N'-tetrakis(2-pyridinylmethyl)-1,2-ethanediamine (TPEN); EDPA; 1,2-bis(o-aminophenoxy)ethane-N,N, N',N'-tetraacetic acid (BAPTA); CaEDTA; EDTA; EGTA; Tricine; ZX1; 4-{[2-(bis-pyridin-2-ylmethylamino)ethylamino]methyl}phenyl)methanesulfonic acid (DPESA); [4-({[2-(bis-pyridin-2-ylmethylamino) ethyl]pyridin-2-ylmethylamino}-methyl)phenyl]methanesulfonic acid (TPESA); and derivatives thereof.

76. The sensor according to any one of paragraphs 53-61, wherein the metal ion is $K^+$.
77. The sensor according to paragraph 76, wherein the chelator or the derivatized chelator is selected from the group consisting of calcium polystyrene sulfonate; sodium polystyrene sulfonate; patiromer; sodium zirconium cyclosilicilate; D-tartrate monobasic; and derivatives thereof.
78. The sensor according to any one of paragraphs 53-61, wherein the metal ion is a heavy metal ion.
79. The sensor according to paragraph 78, wherein the heavy metal ion is selected from the group consisting of $As^{+3}$, $Hg^{+2}$, $Sb^{+3}$, and $Au^+$.
80. The sensor according to paragraph 79, wherein the chelator or the derivatized chelator is selected from the group consisting of Dimercaprol (2,3-dimercapto-1-propanol); Sodium 2,3-dimercaptopropanesulfonate monohydrate; 2,3-Dimercapto-1-propanesulfonic acid sodium salt; and derivatives thereof.
81. A method for the detection of a marker comprising:
    providing a liposome in solution containing a metal ion, the liposome including an antibody configured to bind a target marker; and
    providing a field-effect transistor with a source-drain channel functionalized with a capture antibody to selectively bind to the target marker;
    providing a metal ion chelator or metal ion derivatized chelator in the source-drain channel;
    selectively binding the metal ion chelator or metal ion derivatized chelator with the metal ion in the liposome; and
    causing a change in current in the field-effect transistor as a result of the selective binding the metal ion chelator or metal ion derivatized chelator with the metal ion in the liposome; and
    wherein the detection of the metal ions is indicative of detection of the marker.
82. A method for detection of a marker using a chelator-coated field effect transistor defined on a transistor substrate and having a source-drain channel functionalized with a capture antibody to selectively bind to the marker, the field effect transistor characterized by a conductivity and gain (beta), the method comprising:
    disposing a metal ion chelator or metal ion derivatized chelator in the source-drain channel;
    disposing a liposome containing a metal ion into the source-drain channel of the field effect transistor, the liposome including a detection antibody configured to selectively bind the marker;
    disrupting the liposome to release at least some of the metal ion within the liposome into the source-drain channel of the field effect transistor;
    selectively conjugating the metal ion chelator or metal ion derivatized chelator with the metal ion in the liposome to immobilize the marker on the transistor substrate; and
    washing the source-drain channel of the field effect transistor;
    detecting an amplified detectable current in the field-effect transistor as a result of the selective conjugation of the metal ion chelator or metal ion derivatized chelator with the metal ion in the liposome by changing the conductivity of the field effect transistor and thereby changing the gain (beta) of the field effect transistor,
    whereby detection of metal ions indicative of detection of the marker is achieved.
83. The method of paragraph 82, wherein the limit of detection is improved.
84. The method of any one of paragraphs 81-83, wherein the selective binding of the metal ion chelator or metal ion derivatized chelator with the metal ion in the liposome occurs without substantial interference of the detection of the metal ion by screening by oppositely charged ions and unrelated ions in the solution.
85. The method of any one of paragraphs 81-84, wherein the substrate of the field-effect transistor comprises Gallium Nitride.
86. The method of anyone of paragraphs 81-85, wherein the source and/or the drain channel of the field-effect transistor comprises a material selected from the group of chromium, titanium, copper, aluminum, molybdenum, tungsten, nickel, gold, palladium, platinum, conducting polymers and oligomers, silver paste and combination thereof.
87. The method according to paragraph 86, wherein the source and/or the drain channel of the field-effect transistor comprises a combination of titanium and platinum or a combination of titanium and gold.
88. The method of anyone of paragraphs 81-87, wherein the field-effect transistor further comprises a carbon nanotube.
89. The method according to paragraph 88, wherein the carbon nanotube is at least partially interposed between the source and the drain.
90. The method of any one of paragraphs 81-89, wherein the metal ion is selected from the group consisting of $Ca^{2+}$, $Fe^{2+}$, $Fe^{3+}$, $Mg^{2+}$, $Mn^{2+}$, $Cu^{2+}$, $Cu^{3+}$, $Zn^{2+}$, $Ni^{2+}$, $Co^{2+}$ and a heavy metal ion.
91. The method of anyone of paragraphs 81-89, wherein the metal ion is $Ca^{2+}$.
92. The method according to paragraph 91, wherein the chelator or the derivatized chelator is selected from the group consisting of ethylene glycol-bis(3-aminoethyl ether)-N,N,N',N'-tetraacetic acid (EGTA); ethylene diamine tetra acetic acid (EDTA); N-(2-Hydroxyethyl) ethylenediamine-N, N', N'-triacetic acid Trisodium salt (HEDTA); Nitrilotriacetic acid (NTA); BAPTA; 5,5'-dimethyl BAPTA (tetrapotassium salt); DMNP-EDTA; INDO 1 pentapotassium salt; FURA-2 pentapotassium salt; FURA 2/AM; MAPTAM; FLUO 3 (pentaammonium salt); Tetraacetoxymethyl Bis(2-aminoethyl) Ether N,N,Nprime,Nprime-Tetraacetic Acid; and derivatives thereof.
93. The method according to paragraph 91, wherein the chelator or the derivatized chelator is EGTA or a derivative thereof.
94. The method of anyone of paragraphs 81-89, wherein the metal ion is $Fe^{2+}$ or $Fe^{3+}$.
95. The method according to paragraph 94, wherein the chelator or derivatized chelator is selected from the group consisting of deferasirox; deferiprone; deferoxamine; desferrioxamine; desferrithiocin[2-(3-hydroxypyridin-2-yl)-4-methyl-4,5-dihyrothiazole-4-carboxylic acid; clioquinol; O-trensox (Tris-N-(2-aminoethyl-[8-hydroxyquinoline-5-sulfonato-7-carboxamido] amine); tachpyr (N,N',N"-tris(2-pyridylmethyl)-cis,cis-1,3,5-triamino-cyclohexane); dexrazoxane; triapine (3-aminopyridine-2-carboxaldehyde thiosemicarbazone); pyridoxal isonicotinoyl hydrazone; di-2-pyridylketone thiosemicarbazone series; flavan-3-ol; curcumin; apocynin; kolaviron; floranol; baicalein; baicalin; *Ligusticum wallichi* Francha (ligustrazine); quercetin; epigallocatechin gallate; theaflavin; phytic acid; genistein (5,7,4'-tri-hydroxyisoflavone); EDTA; NTA; HBED, o-Phenanthroline monohydrate; Pyridoxal Isonicotinoyl Hydrazone, 2,2prime-Dipyridyl, (S)-1-(p-Bromoacetamidobenzyl)ethylenediaminetetraacetic Acid, (S)-1-(4-Aminoxyacetamidobenzyl)ethylenediaminetetraacetic Acid; and derivatives thereof.

96. The method of anyone of paragraphs 81-89, wherein the metal ion is $Mg^{2+}$.

97. The method according to paragraph 96, wherein the chelator or the derivatized chelator is selected from the group consisting of EDTA, EGTA, HEDTA, NTA and derivatives thereof.

98. The method of anyone of paragraphs 81-89, wherein the metal ion is $Mn^{2+}$.

99. The method according to paragraph 98, wherein the chelator or the derivatized chelator is selected from the group consisting of EDTA; EGTA; HEDTA; NTA; triethylenetetramine-N,N,N',N'',N''',N'''-hexaacetic acid (TTHA); diethylenetriaminepentaacetic acid (DTPA); DPTA; DPTA-OH; HBED; and derivatives thereof 100. The method of any one of paragraphs 81-89, wherein the metal ion is $Cu^{2+}$ or $Cu^{3+}$.

101. The method according to paragraph 100, wherein the chelator or the derivatized chelator is selected from the group consisting of EDTA; NTA; D-Penicillamine (DPA); Tetraethylenetetraamine (TETA); clioquinol and derivatives thereof.

102. The method of any one of paragraphs 81-89, wherein the metal ion is $Zn^{2+}$.

103. The method according to paragraph 102, wherein the chelator or the derivatized chelator is selected from the group consisting of ADAMTS-5 Inhibitor; N,N,N',N'-tetrakis(2-pyridinylmethyl)-1,2-ethanediamine (TPEN); EDPA; 1,2-bis(o-aminophenoxy)ethane-N,N, N',N'-tetraacetic acid (BAPTA); CaEDTA; EDTA; EGTA; Tricine; ZX1; 4-{[2-(bis-pyridin-2-ylmethylamino)ethylamino]methyl}phenyl)methanesulfonic acid (DPESA); [4-({[2-(bis-pyridin-2-ylmethylamino) ethyl]pyridin-2-ylmethylamino}-methyl)phenyl]methanesulfonic acid (TPESA); and derivatives thereof.

104. The method of any one of paragraphs 81-89, wherein the metal ion is $K^+$.

105. The method according to paragraph 104, wherein the chelator or the derivatized chelator is selected from the group consisting of calcium polystyrene sulfonate; sodium polystyrene sulfonate; patiromer; sodium zirconium cyclosilicilate; D-tartrate monobasic; and derivatives thereof.

106. The method of any one of paragraphs 81-89, wherein the metal ion is a heavy metal ion.

107. The method according to paragraph 106, wherein the heavy metal ion is selected from the group consisting of $As^{+3}$, $Hg^{+2}$, $Sb^{+3}$, and $Au^+$.

108. The method according to paragraph 107, wherein the chelator or the derivatized chelator is selected from the group consisting of Dimercaprol (2,3-dimercapto-1-propanol); Sodium 2,3-dimercaptopropanesulfonate monohydrate; 2,3-Dimercapto-1-propanesulfonic acid sodium salt; and derivatives thereof.

109. The method of any one of paragraphs 81-108, wherein the marker is a biomarker, an environmental marker, an allergen, or a microorganism.

110. The method of any one of paragraphs 81-109, wherein the metal ion is released from the liposome by contacting the liposome with a detergent.

DETAILED DESCRIPTION OF THE DISCLOSURE

Figure 1:
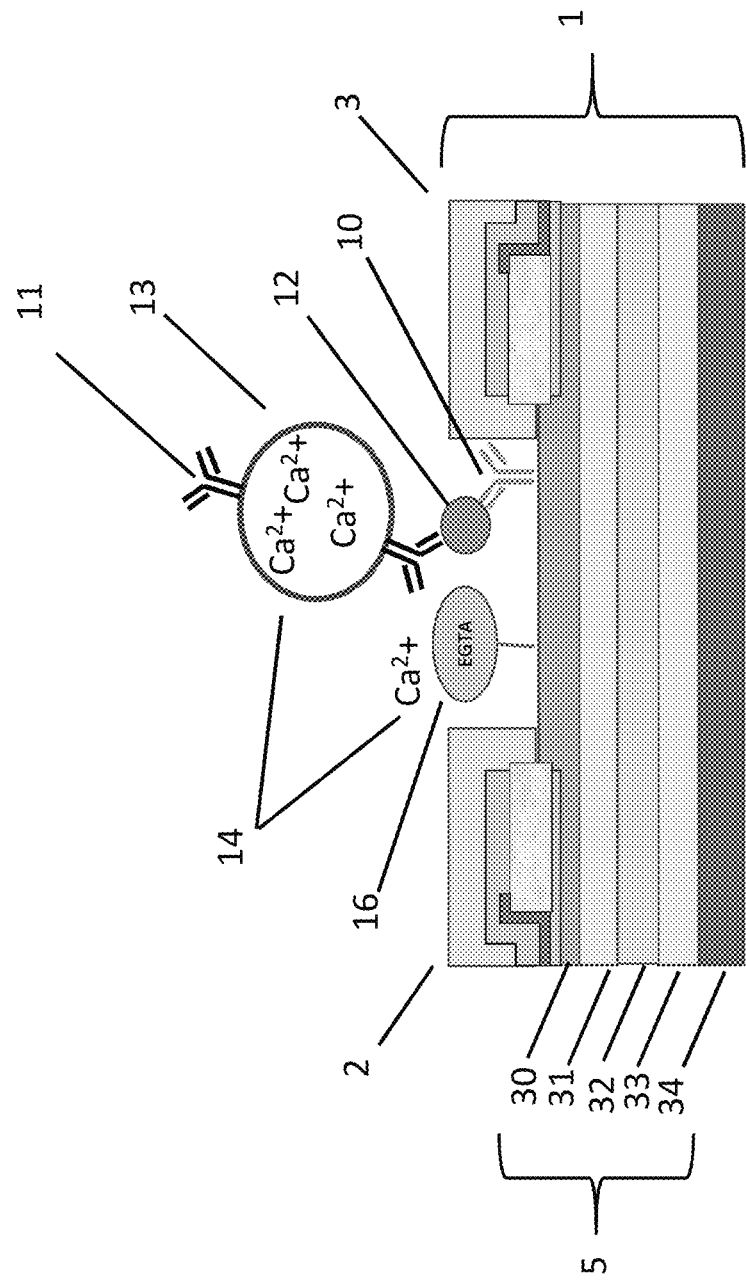
FIG. 1 shows a schematic side cross sectional representation of a transistor device and liposome immunoassay in accordance with embodiments of the present disclosure.

The ability to detect very rare cells or markers at low concentrations in a sample, such as blood or plasma, with accuracy and sensitivity is still a significant problem for molecular diagnostics. Typical protein detection methods, such as ELISAs, are generally not sensitive enough to detect low concentrations of important biological markers. There is a need for cost-effective and rapid analysis methods and devices for the detection of markers, including biomarkers and environmental markers, especially more sensitive, specific, and robust methods and devices.

The present disclosure provides a sensitive, specific, and robust FET and devices comprising said FET, which can be used to specifically detect markers that are present at a low concentration in the sample, near or below the limit of detection (LOD), such that amplification is necessary. The FET may be used in a cost-effective and rapid analysis system for detection of markers or microorganisms, which maintains a high specificity and sensitivity, and can be used, e.g. in the field.

The LOD of a detection method is the lowest amount of analyte or marker in a sample which can be detected. Accordingly, an improved LOD when the amount of the analyte or marker in the sample which can be detected is decreased or the LOD is reduced. Several approaches for determining the detection limit are possible. For instance, in the detection of bacteria, every test method will have an upper and lower LOD. This is determined by the statistical accuracy with which the analysts are able to count the colonies growing on the plates.

The FET of the present disclosure permits the detection of markers at very low concentration, which may be due to (a) the immobilization of the marker near the FET and by (b) amplifying the signal. The immobilization may be accomplished by functionalizing the FET with a capture molecule, e.g. a capture antibody, that binds the marker. The amplification step may involve binding the immobilized marker with a detection molecule comprising an amplifiable signal. For example, a detection antibody that binds the marker at a different epitope than the capture antibody may be conjugated to the amplifiable signal. After the detection molecule, e.g. detection antibody, is bound to the immobilized marker, the FET can optionally be washed to remove any unbound detection molecule. In some embodiments, the amplifiable signal is a liposome comprising an ion, e.g. a metal ion, and the signal is amplified by releasing the ions from the liposomes, e.g. using a detergent. The signal may be further amplified by functionalizing the FET surface with a chelator (or a derivatized chelator), which amplifies the ionic signal by attracting the ions toward the FET device. Preferably, the chelator (or derivatized chelator) specifically binds the metal ion present, e.g., in the lipid vesicle.

1. General Techniques

Unless otherwise defined herein, scientific and technical terms used in this application shall have the meanings that are commonly understood by those of ordinary skill in the art. Generally, nomenclature used in connection with, and the laboratory procedures techniques performed in pharmacology, cell and tissue culture, analytical chemistry, biochemistry, synthetic organic chemistry, medicinal and pharmaceutical chemistry, molecular biology, cell and cancer biology, neurobiology, neurochemistry, virology, immunology, microbiology, genetics and protein and nucleic acid chemistry, described herein, are those well-known and commonly used in the art. Standard techniques are used for chemical syntheses and chemical analyses. In case of conflict, the present specification, including definitions, will control.

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Sambrook and Russell, Molecular Cloning: A Laboratory Manual, 3rd. ed., Cold Spring Harbor Laboratory Press, Cold Spring Harbor, NY (2001); Ausubel et al., Current Protocols in Molecular Biology, John Wiley & Sons, NY (2002); Harlow and Lane Using Antibodies: A Laboratory Manual, Cold Spring Harbor Laboratory Press, Cold Spring Harbor, NY (1998); Coligan et al., Short Protocols in Protein Science, John Wiley & Sons, NY (2003); Short Protocols in Molecular Biology (Wiley and Sons, 1999).

Enzymatic reactions and purification techniques are performed according to manufacturer's specifications, as commonly accomplished in the art or as described herein.

Throughout this specification, aspects and embodiments, the word "comprise", or variations such as "comprises" or "comprising", will be understood to imply the inclusion of a stated integer or group of integers, but not the exclusion of any other integer or group of integers. The term "including" is used to mean "including but not limited to". "Including" and "including but not limited to" are used interchangeably.

It is understood that wherever embodiments or aspects are described herein with the language "comprising", otherwise analogous embodiments described in terms of "consisting of" and/or "consisting essentially of" are also provided.

Any example(s) following the term "e.g." or "for example" is not meant to be exhaustive or limiting.

Unless otherwise required by context, singular terms shall include pluralities and plural terms shall include the singular.

The articles "a", "an" and "the" are used herein to refer to one or to more than one (i.e., to at least one) of the grammatical object of the article. By way of example, "an element" means one element or more than one element. As used herein, the term "about" modifying the quantity of an ingredient, parameter, calculation, or measurement in the compositions of the disclosure or employed in the methods of the disclosure refers to a variation in the numerical quantity that can occur, for example, through typical measuring and liquid handling procedures used for making isolated polypeptides or pharmaceutical compositions in the real world; through inadvertent error in these procedures; through differences in the manufacture, source, or purity of the ingredients employed to make the compositions or carry out the methods; and the like without having a substantial effect on the chemical or physical attributes of the compositions or methods of the disclosure. Such variation can be within an order of magnitude, typically within 10% of a given value or range, more typically still within 5% of a given value or range. Reference to "about" a value or parameter herein includes (and describes) embodiments that are directed to that value or parameter per se. For example, description referring to "about X" includes description of "X". Numeric ranges are inclusive of the numbers defining the range.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g., 1 to 6.1, and ending with a maximum value of 10 or less, e.g., 5.5 to 10.

Where aspects or embodiments of this disclosure are described in terms of a Markush group or other grouping of alternatives, the present disclosure encompasses not only the entire group listed as a whole, but each member of the group individually and all possible subgroups of the main group, but also the main group absent one or more of the group members. The present disclosure also envisages the explicit exclusion of one or more of any of the group members in the embodiments of the invention.

Exemplary methods and materials are described herein, although methods and materials similar or equivalent to those described herein can also be used in the practice or testing of the present disclosure. The materials, methods, and examples are illustrative only and not intended to be limiting.

2. Definitions

The term "antibody," as used herein, refers to a gamma-globulin, or a fragment thereof, that exhibits a specific binding activity for a target molecule, namely "antigen". The term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, and chimeric antibodies. Such antibodies may be produced in a variety of ways, including hybridoma cultures, recombinant expression in bacteria or mammalian cell cultures, and recombinant expression in transgenic animals. Also, antibodies can be produced by selecting a sequence from a library of sequences expressed in display systems such as filamentous phage, bacterial, yeast or ribosome. There is abundant guidance in the literature for selecting a particular production methodology, e.g., Chadd and Chamow, Curr. Opin. Biotechnol., 12:188-194 (2001). The choice of manufacturing methodology depends on several factors including the antibody structure desired, the importance of carbohydrate moieties on the antibodies, ease of culturing and purification, and cost. Many different antibody structures may be generated using standard expression technology, including full-length antibodies, antibody fragments, such as Fab and Fv fragments, as well as chimeric antibodies comprising components from different species.

The term "antibody," as used herein, also includes the term "antigen binding fragment," which refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')2, and Fv fragments. Antibody fragments of small size, such as Fab and Fv fragments, having no effector functions and limited pharmacokinetic activity, may be generated in a bacterial expression system. Single chain Fv fragments show low immunogenicity and are cleared rapidly from the blood.

As used herein, a "capture molecule" is a molecule used to bind an antigen or marker being assayed via an affinity binding between the capture molecule and the antigen or marker in a liquid phase and affix or immobilize the captured antigen or marker to a solid phase. The capture molecule may comprise an antibody, a recombinant antibody, a protein, a recombinant protein, small or big organic molecules, or peptide or nucleic acid aptamers. If the capture molecule is an antibody, then it is named as "capture antibody." The capture molecule may be affixed to the solid phase. In some embodiments, the capture molecule is capable of being affixed to the solid phase, e.g., upon cycling of a magnetic field or an electric current.

The terms "chelator" and "chelating agent" are used interchangeable herein and refer to a molecule that binds to metal ions and form a complex. The affinity of the chelating agent for the metal ion is measured by the dissociation constant or $K_D$. As used herein, a high-affinity chelator is typically a binding with an affinity corresponding to a $K_D$ of about $10^{-8}$ M or less, about $10^{-9}$ M or less, about $10^{-10}$ M or less, or about $10^{-11}$ M or less. $K_D$ values are measured by techniques known by the skilled in the art, such as, the pH metric method developed by Moisescu and Pusch (Moisescu, D. G. and Pusch, H. (1975) Pfluegers Arch. 355, 243) or a modified version of said pH metric method (Smith and Miller. (1985). Biochimica et Biophysica Acta; Vol. 839, Issue 3, 287-299).

The terms "derivatized chelator" and "derivatized chelating agent" are used interchangeable herein and refer to chelators that have been chemically altered to permit them to be interposed onto a field effect transistor or a component thereof, including a substrate, a carbon nanotube, a dielectric material, a gate, or between a source and a drain. Methods for derivatizing chelators for such disposition are known in the art. For example, pyrenes are known to adsorb to carbon nanotube surfaces through π-π interactions. Additionally, azide chemistry has been demonstrated to be a powerful means to covalently modify carbon nanotubes.

As used herein, the term "calcium chelator" is used to refer to molecules that are able to bind calcium in a selective way, because they have higher affinity for calcium than for any other metal ions. Binding to calcium is performed through carboxylic groups.

As used herein, the term "iron chelators" is used to refer to molecules that are able to bind iron in a selective way, because they have higher affinity for iron than for any other metal ions. They typically contain oxygen, nitrogen or sulfur-donor atoms that form coordinate bonds with bound iron. The donor atoms of the ligand affect the preference of the chelator for either the Fe(II) or Fe(III) oxidation states.

As used herein, the "Debye length" (also called Debye radius), named after Peter Debye, is a measure of a charge carrier's net electrostatic effect in a solution and how far its electrostatic effect persists. A Debye sphere is a volume whose radius is the Debye length. With each Debye length, charges are increasingly electrically screened. Every Debye-length $X_D$, the electric potential will decrease in magnitude by 1/e. Specifically, in physiological solution environments, which are relevant to many important biological, medical, and diagnostic applications, the short screening length, <1 nm, reduces the field produced by charged biomolecules at FET surface and thus makes real-time label-free detection difficult. This short screening length is also called "Debye limit" or "Debye screening limitation".

The term "detectable label", as used in the present disclosure, refers to a molecule with a physical property or biochemical activity that is analyzable by a detector via the label's physical property or the label's catalyzed activity.

The term "detection molecule", as used in the present disclosure, refers to a molecule that selectively binds to a marker and is conjugated to an amplifiable signal. The detection molecule may comprise an antibody, a recombinant antibody, a protein, a recombinant protein, small or big organic molecules, or peptide or nucleic acid aptamers. If the detection molecule is an antibody, then it is named as "detection antibody." Optionally, the amplifiable signal is a lipid vesicle comprising ions, preferably metal ions. In some embodiments, the ions are released from the lipid vesicle by contacting it with a detergent, such as a non-ionic detergent.

The term "detergent," as used herein, refers to a surfactant or a mixture of surfactants. Examples of surfactants include, but not limited to, anionic surfactants, non-ionic surfactants, cationic surfactants, amphoteric surfactants (including betaine surfactants and zwitterionic surfactants) and mixtures thereof.

The term "dielectric material", as used herein, refers to an electrical insulator that can be polarized by an applied electric field. When a dielectric material is placed in an electric field, electric charges do not flow through the material as they do in an electrical conductor but only slightly shift from their average equilibrium positions causing dielectric polarization. A perfect dielectric material is a material with zero electrical conductivity, exhibiting only a displacement current. Therefore, it stores and returns electrical energy as if it were an ideal capacitor. The dielectric constant of a material, also called the permittivity of a material, represents the ability of a material to concentrate electrostatic lines of flux. In more practical terms, it represents the ability of a material to store electrical energy in the presence of an electric field.

The term "Field Effect Transistor (FET)", as used herein, refers to a transistor that uses an electric field to control the electrical behavior of the device. FET consists of three electrodes: source, drain, and gate. The positive gate voltage attracts electrons from the bulk to the surface of the substrate. A sufficient number of electrons induced form a thin n-channel by electrically bridging the source and drain. Otherwise, when a specific molecular recognition occurs on the gate, the FET detects the change of charge density at the interface by an electrostatic interaction with the electrons in the n-channel. A skilled person in the art will be able to determine the materials coated on the surface of the gate insulator of the FET.

The term "lipid vesicle," as used in the present application, refers to spherical bilayers which are comprised of one or more lipids. As used herein, the lipid vesicles of the invention may also be referred to as "liposomes". The type, number and ratio of lipids may vary with the proviso that collectively they form spherical bilayers or vesicles. The lipids may be isolated from a naturally occurring source or they may be synthesized apart from any naturally occurring source. There are three main types of lipid vesicles: (1) a multilamellar vesicle (MLV), with several lamellar phase lipid bilayers; (2) a small unilamellar liposome vesicle (SUV) with one lipid bilayer and a diameter typically ranging between 15-30 nm and (3) a large unilamellar vesicle (LUV) with one lipid bilayer and a diameter typically ranging between 100-200 nm or larger. Lipid vesicles may be disrupted by contacting them with, e.g., a detergent. Optionally, the detergent is a non-ionic detergent.

The terms "marker" and "analyte" are used interchangeably herein and refer to one or more molecules that are differentially present in a sample and that are indicators of the presence of an event, condition or process. The term "biomarker", as used herein, refers to one or more biological molecules that are differentially released into a biological fluid by any means (including secretion or by leakage through the cell membrane). The term "biomarker" refers to a distinctive biological or biologically derived indicator of a process, event or condition. Analyte biomarkers can be used in methods of diagnosis, e.g. clinical screening, and prognosis assessment and in monitoring the results of therapy, identifying patients most likely to respond to a particular therapeutic treatment, drug screening and development.

Diagnostically useful biomarkers are identified using measured levels of a single biomarker obtained from a statistically significant number of disease-negative and disease-positive subjects in a population and establishing a mean and a standard deviation for the disease negative and positive states.

A "microfluidics device" or "biochip", as used herein, refers to a device or system that has channels and/or chambers that are generally fabricated on the micron or submicron scale. The typical channels or chambers have at least one cross-sectional dimension in the range of about 0.1 microns to about 500 microns. The microfluidic device comprises multiple "microfluidic channel blocks", with fluid flow between said blocks being selectively operable. In the context of the present application, a "block" may be defined as a discrete area on the device having a microfluidic channel with a long path within a confined space.

The term "sample", as used herein, can refer to a fluid wherein markers or biomarkers are present, or a fluid derived from the specimen into which the markers or biomarkers are initially present. In one embodiment, the sample is a biological sample into which biomarkers are released, or a fluid derived from the biological sample into which biomarkers are initially released. Such derivation may occur either in vivo or in vitro. In some instances, the biological sample is a circulating fluid such as blood or lymph, or a fraction thereof, such as serum or plasma. In other cases, the biological sample remains substantially in a particular locus, for example, synovial fluid, cerebrospinal fluid or interstitial fluid. In still further cases, the biological fluid is an excreted fluid, for example, urine, breast milk, saliva, sweat, tears, mucous, nipple aspirants, semen, vaginal fluid, pre-ejaculate and the like. A biological fluid also refers to a liquid in which cells are cultured in vitro such as a growth medium, or a liquid in which a cell sample is homogenized, such as a buffer. In some cases, the sample is a food sample or an environmental sample, such as a water or a soil sample, which contains markers or molecules to be detected.

3. Capture Antibodies and Antibody-Lipid Vesicle Conjugates

In some embodiments, the field-effect transistor comprises a capture molecule. Optionally, the capture molecule is an antibody (the capture antibody) or a derivatized capture antibody. In some embodiments, the capture molecule (e.g. capture antibody or derivatized capture antibody) is at least partially interposed in the substrate. Optionally, the capture molecule (e.g. capture antibody or derivatized capture antibody) is at least partially interposed between the source and the drain. Preferably, the capture molecule (e.g. capture antibody or derivatized capture antibody) is configured to selectively bind a marker and immobilize it to the FET.

The immobilized maker may then be contacted with a detection molecule. Optionally, the detection molecule is a detection antibody. In some embodiments, the detection molecule (e.g., detection antibody) is linked to an amphiphilic lipid vesicle or liposome, wherein the vesicle comprises a detectable label. The detectable label may be an ion, preferably a metal ion. Optionally, the FET is functionalized with a chelator or derivatized chelator that selectively binds the ion in the lipid vesicle. In some embodiments, the marker bound detection molecule is washed to remove any unbound detection molecule. The ions may be released from the lipid vesicle by contacting the lipid vesicle with a detergent. Optionally, the detergent is a non-ionic detergent.

Methods for derivatizing antibodies to permit disposition onto surfaces of the FET are known in the art. Non-limiting examples for conjugating the antibodies to the substrate between the source and the drain include, but are not limited to, (1) crosslinking through sulfhydryl-reactive groups by reacting a thiol group of the antibody (such as the ones present in Cysteine) with any sulfhydryl-reactive chemical groups, including haloacetyls, maleimides, aziridines, acryloyls, arylating agents, vinylsulfones, pyridyl disulfides, TNB-thiols and disulfide reducing agents; (2) 1-Pyrenebutyric acid N-hydroxysuccinimide ester (pyrene-NHS). Pyrenes are hydrophobic polycyclic aromatics that bind avidly to the FET substrate and they do not adversely affect the electrical properties of the substrate (see, for example, Stefansson et al. Journal of Nanotechnology, vol. 2012, Article ID 490175, 2012), incorporated herein by reference in its entirety; and (3) through biomolecules such as biotin/streptavidin. In some embodiments, the capture antibody or derivatized capture antibody is at least partially interposed on a surface containing gold.

4. Metal Ions, Chelators, and Derivatized Chelators

The instant disclosure relates to field effect transistors (FETs), sensors comprising FETs, devices comprising such sensors and FETs and methods using FETs to detect markers or metal ions. In some embodiments, the FET comprises a chelator or a derivatized chelator. The chelator may be a metal ion chelator or a derivatized metal ion chelator. Optionally, the chelator or the derivatized chelator is deposited on the surface of the FET and is configured to contact a detectable label. In some embodiments, the detectable label comprises an ion, e.g. a metal ion. Non-limiting examples of metal ions include iron ions, copper ions, cobalt ions, manganese ions, chromium ions, nickel ions, zinc ions, cadmium ions, molybdenum ions, lead ions, and the like. In any of the FETs, sensors, devices, or methods disclosed herein, the metal ion being detected is, optionally, selected from the group consisting of $Ca^{2+}$, $Fe^{2+}$, $Fe^{3+}$, $Mg^{2+}$, $Mn^{2+}$, $Cu^{2+}$, $Cu^{3+}$, $Zn^{2+}$, $Ni^{2+}$, $Co^{2+}$ and a heavy metal ion (e.g., $As^{+3}$, $Hg^{+2}$, $Sb^{+3}$, and $Au^{+}$). Preferably, the metal ions to be detected are divalent and trivalent ions.

In some embodiments, chelating agents of metallic ions include chelating agents of $Ca^{2+}$, $Fe^{2+}$, $Fe^{3+}$, $Mg^{2+}$, $Mn^{2+}$, $Cu^{2+}$, $Cu^{3+}$, $Zn^{2+}$, $Ni^{2+}$, $Co^{2+}$, heavy metal ions (e.g., $As^{+3}$, $Hg^{+2}$, $Sb^{+3}$, and $Au^{+}$), and the like. It is within the skill of the art to select a chelating agent or derivatized chelating agent that will bind or complex with a particular ion of interest. See, e.g., Bers D. M., MacLeod K. T. (1988) Calcium Chelators and Calcium Ionophores. In: Baker P. F. (eds) Calcium in Drug Actions. Handbook of Experimental Pharmacology, vol 83. Springer, Berlin, Heidelberg; Hatcher, H C. et al. *Future Med Chem.* 2009 December; 1(9): 10.4155; Sheth, S., *Curr Opin Hematol* 2014, 21:179; Missy P. et al. *Hum Exp Toxicol.*, 2000, vol. 19(8): 448-456; Sigma Aldrich, BioUltra Reagents: Chelators (available at https://www.sigmaaldrich.com/life-science/metabolomics/bioultra-reagents/chelators.html); Santa Cruz Biotechnology Chelators (available at https://www.scbt.com/scbt/browse/chelators/_/N-lazot5l); Lawson M K, et al. *Curr Pharmacol Rep* (2016) 2:271-280; Radford and Lippard, *Curr Opin Chem Biol.* 2013 April; 17(2): 129-136; Chaitman, M. et al., P T. 2016 January; 41(1): 43-50, each of which is incorporated herein in its entirety.

In some embodiments, the chelating agent or derivatized chelating agent selectively binds a metal ion. Preferably, the chelating agent or derivatized chelating agent selectively binds the metal ion contained within the lipid vesicle of a detection molecule, such as a detection antibody. Optionally, the chelating agent or derivatized chelating agent binds several metal ions. The chelating agent or derivatized chelating agent may preferentially bind one metal ion, but still bind other metal ions. In some embodiments, the chelator is a custom designed chelator.

In some embodiments, the chelator is selected from the group consisting of 1,1,1-Trifluoroacetylacetone; 1,4,7-Trimethyl-1,4,7-triazacyclononane; 2,2'-Bipyrimidine; Acetylacetone; Alizarin; Amidoxime; Amidoxime group; Aminoethylethanolamine; Aminomethylphosphonic acid; Aminopolycarboxylic acid; ATMP; BAPTA; Bathocuproine; BDTH2; Benzotriazole; Bidentate; Bipyridine; 2,2'-Bipyridine; Bis(dicyclohexylphosphino)ethane; 1,2-Bis(dimethylarsino)benzene; 1,2-Bis(dimethylphosphino)ethane; 1,2-Bis(diphenylphosphino)ethane; Calixarene; Carcerand; Catechol; Cavitand; Chelating resin; Chelex 100; Citrate; Citric acid; Clathrochelate; Corrole; Cryptand; 2.2.2-Cryptand; Cyclam; Cyclen; Cyclodextrin; Deferasirox; Deferiprone; Deferoxamine; Denticity; Dexrazoxane; Diacetyl monoxime; Trans-1,2-Diaminocyclohexane; 1,2-Diaminopropane; 1,5-Diaza-3,7-diphosphacyclooctanes; 1,4-Diazacycloheptane; Dibenzoylmethane; Diethylenetriamine; Diglyme; 2,3-Dihydroxybenzoic acid; Dimercaprol; 2,3-Dimercapto-1-propanesulfonic acid; Dimercaptosuccinic acid; 1,1-Dimethylethylenediamine; 1,2-Dimethylethylenediamine; Dimethylglyoxime; DIOP; Diphenylethylenediamine; 1,5-Dithiacyclooctane; Domoic acid; DOTA; DOTA-TATE; DTPMP; EDDHA; EDDS; EDTA; EDTMP; EGTA; 1,2-Ethanedithiol; Ethylenediamine; Ethylenediaminediacetic acid; Ethylenediaminetetraacetic acid; Etidronic acid; Fluo-4; Fura-2; Gallic acid; Gluconic acid; Glutamic acid; Glyoxal-bis(mesitylimine); Glyphosate; Hexafluoroacetylacetone; Homocitric acid; Iminodiacetic acid; Indo-1; Isosaccharinic acid; Kainic acid; Ligand; Malic acid; Metal acetylacetonates; Metal dithiolene complex; Metallacrown; Nitrilotriacetic acid; Oxalic acid; Oxime; Pendetide; Penicillamine; Pentetic acid; Phanephos; Phenanthroline; O-Phenylenediamine; Phosphonate; Phthalocyanine; Phytochelatin; Picolinic acid; Polyaspartic acid; Porphine; Porphyrin; 3-Pyridylnicotinamide; 4-Pyridylnicotinamide; Pyrogallol; Salicylic acid; Sarcophagine; Sodium citrate; Sodium diethyldithiocarbamate; Sodium polyaspartate; Terpyridine; Tetramethylethylenediamine; Tetraphenylporphyrin; Thenoyltrifluoroacetone; Thioglycolic acid; TPEN; 1,4,7-Triazacyclononane; Tributyl phosphate; Tridentate; Triethylenetetramine; Triphos; Trisodium citrate; 1,4,7-Trithiacyclononane; and TTFA and derivatives thereof.

In some embodiments, the metal ion is $Ca^{2+}$. Optionally, the chelator or the derivatized chelator for $Ca^{2+}$ is selected from the group consisting of ethylene glycol-bis(R-aminoethyl ether)-N,N,N',N'-tetraacetic acid (EGTA); ethylene diamine tetra acetic acid (EDTA); N-(2-Hydroxyethyl)ethylenediamine-N, N', N'-triacetic acid Trisodium salt (HEDTA); Nitrilotriacetic acid (NTA); BAPTA; 5,5'-dimethyl BAPTA (such as tetrapotassium salt); DMNP-EDTA; INDO 1 (such as pentapotassium salt); FURA-2 (such as pentapotassium salt); FURA 2/AM; MAPTAM; FLUO 3 (such as pentaammonium salt); Tetraacetoxymethyl Bis(2-aminoethyl) Ether N,N,N',N'-Tetraacetic Acid; 2-{(carboxymethyl) 2-trimethylamino ethyl amino}acetic acid and salts of such agents, as well as free acids, derivatives and combinations thereof. Preferably, the chelator or the derivatized chelator for $Ca^{2+}$ is EGTA or a derivative thereof.

Methods to determine the calcium binding affinity of EGTA are known in the art. A non-limiting example of such method is the Bers method (Bers DM. Am J Physiol. 1982; 242(5):C404-8), incorporated by reference herein in its entirety, wherein free $Ca^{2+}$ in Ca-EGTA solutions are measured with a Ca electrode, bound Ca is calculated, and Scatchard and double-reciprocal plots are resolved for the total EGTA and the apparent Ca-EGTA association constant ($K_{app}$) in the solutions used. The free $Ca^{2+}$ is then recalculated using the determined parameters, giving a more accurate knowledge of the free $Ca^{2+}$ in these solutions and providing an accurate calibration curve for the Ca electrode. This method allows determination of free $Ca^{2+}$, $K_{app}$, and total EGTA in the actual solutions used regardless of pH, temperature, or ionic strength.

In some embodiments, the metal ion is $Fe^{2+}$ or $Fe^{3+}$. Optionally, the chelator or derivatized chelator for $Fe^{2+}$ or $Fe^{3+}$ is selected from the group consisting of deferasirox; deferiprone; deferoxamine; desferrioxamine; desferrithiocin [2-(3-hydroxypyridin-2-yl)-4-methyl-4,5-dihyrothiazole-4-carboxylic acid; clioquinol; O-trensox (Tris-N-(2-aminoethyl-[8-hydroxyquinoline-5-sulfonato-7-carboxamido] amine); tachpyr (N,N',N''-tris(2-pyridylmethyl)-cis,cis-1,3,5-triamino-cyclohexane); dexrazoxane; triapine (3-aminopyridine-2-carboxaldehyde thiosemicarbazone); pyridoxal isonicotinoyl hydrazone; di-2-pyridylketone thiosemicarbazone series; flavan-3-ol; curcumin; apocynin; kolaviron; floranol; baicalein; baicalin; Ligusticum wallichi Francha (ligustrazine); quercetin; epigallocatechin gallate; theaflavin; phytic acid; genistein (5,7,4'-tri-hydroxyisoflavone); EDTA; NTA; HBED, o-Phenanthroline monohydrate; Pyridoxal Isonicotinoyl Hydrazone, 2,2prime-Dipyridyl, (S) 1 (p Bromoacetamidobenzyl) ethylenediaminetetraacetic Acid, (S) 1 (4 Aminoxyacetamidobenzyl)ethylenediaminetetraacetic Acid; Lipoic Acid and salts of such agents, as well as the free acids, derivatives thereof and combinations thereof.

In some embodiments, the metal ion is $Mg^{2+}$. Optionally, the chelator or the derivatized chelator for $Mg^{2+}$ is selected from the group consisting of EDTA, EGTA, HEDTA, NTA and salts of such agents, as well as the free acids, derivatives thereof and combinations thereof.

In some embodiments, the metal ion is $Mn^{2+}$. Optionally, the chelator or the derivatized chelator for $Mn^{2+}$ is selected from the group consisting of EDTA; EGTA; HEDTA; NTA; triethylenetetramine-N,N,N',N'',N''',N'''-hexaacetic acid (TTHA); para-aminosalicylic acid (PAS), 1,2-cyclohexylenedinitrilotetraacetic acid (CDTA), nitrilotriacetic acid (NAS), diethylenetriaminepentaacetic acid (DTPA); DPTA-OH; HBED; and salts of such agents, as well as the free acids, derivatives thereof and combinations thereof.

In some embodiments, the metal ion is $Cu^{2+}$ or $Cu^{3+}$. Optionally, the chelator or the derivatized chelator for $Cu^{2+}$ or $Cu^{3+}$ is selected from the group consisting of EDTA; NTA; D-Penicillamine (DPA); Tetraethylenetetraamine (TETA); clioquinol; glutamic acid; lipoic acid; and salts of such agents, as well as the free acids, derivatives thereof and combinations thereof.

In some embodiments, the metal ion is $Zn^{2+}$. Optionally, the chelator or the derivatized chelator for $Zn^{2+}$ is selected from the group consisting of ADAMTS-5 Inhibitor; N,N,N',N'-tetrakis(2-pyridinylmethyl)-1,2-ethanediamine (TPEN); EDPA; 1,2-bis(o-aminophenoxy)ethane-N,N,N',N'-tetraacetic acid (BAPTA); CaEDTA; EDTA; EGTA; Tricine; ZX1; 4-{[2-(bis-pyridin-2-ylmethylamino)ethylamino]methyl}phenyl)methanesulfonic acid (DPESA); [4-({[2-(bis-pyridin-2-ylmethylamino)ethyl]pyridin-2-ylmethylamino}-methyl)phenyl]methanesulfonic acid (TPESA); and derivatives thereof.

In some embodiments, the metal ion is $Ni^{2+}$. Optionally, the chelator or the derivatized chelator for $Ni^{2+}$ is selected from the group consisting of citrate, malate, histidine, EDTA, sodium diethyldithiocarbamate (Dithiocarb), dimethyldithiocarbamate, diisopropyl, morpholine-I-dithiocarbamate, N,N'-ethylene-bis-dithiocarbamate, 2-2(oxo-1-imidazo-lidyl) ethyldithiocarbamate, dithiocarbamate, tetraethylthiuram (Antabuse), d-penicillamine, dimercaprol (BAL), N-methyl formamide, 8-Hydroxyquinoline-Cyclodextrin Conjugate, glutamic acid and salts of such agents, as well as the free acids, derivatives thereof and combinations thereof. In some embodiments the chelator or derivatized chelator for $Ni^{2+}$ is a nickel binding protein. See, e.g., Sudan R J J, et al. (2015) Ab Initio Coordination Chemistry for Nickel Chelation Motifs. PLoS ONE 10(5): e0126787. doi: 10.1371/journal.pone.0126787, incorporated by reference herein in its entirety.

In some embodiments, the metal ion is $Co^{2+}$. Optionally, the chelator or the derivatized chelator for $Co^{2+}$ is selected from the group consisting of L-cysteine; L-methionine; N-acetyl-cysteine; EDTA; sodium 2,3-dimercaptopropane sulfonate (DMPS); diethylenetriaminepentaacetic acid (DTPA); 2,3-dimercaptosuccinic acid (DMSA); dimercaprol; 8-Hydroxyquinoline-Cyclodextrin Conjugate; glutamic acid; deferasirox; desferrioxamine; deferiprone; and salts of such agents, as well as the free acids, derivatives thereof and combinations thereof.

In some embodiments, the metal ion is a heavy metal ion. Optionally, the heavy metal ion is selected from the group consisting of $As^{+3}$, $Hg^{+2}$, $Sb^{+3}$, and $Au^{+}$. In some embodiments, the chelator or the derivatized chelator for the heavy metal ion is selected from the group consisting of Dimercaprol (2,3-dimercapto-1-propanol); Sodium 2,3 dimercaptopropanesulfonate monohydrate; 2,3-Dimercapto-1-propanesulfonic acid sodium salt; Dimercaptosuccinic acid; Penicillamine; Lipoic Acid; and salts of such agents, as well as the free acids, derivatives thereof and combinations thereof. In some embodiments, the chelator or derivatized chelator for $Au^{+}$ comprises an SH group. Optionally, the chelator or derivatized chelator for $Hg^{2+}$ comprises an SH group.

Methods for adding a thiol group to the chelator are known in the art. Non-limiting examples include, but are not limited, to: (a) Potassium thioacetate was added into a solution of 1,4-diioidobutane to afford the corresponding thioester. The thioester is added to a dilute solution of $K_4EGTA$, resulting in the formation of the mono-functionalized thioester-$K_3EGTA$. Thioester-$K_3EGTA$ then reacts with KOH followed by neutralization with HCl to afford EGTA-SH; (b) Addition of 2-aminoethane-1-thiol to a solution of protected EGTA; and (c) Reaction of EGTA with 1-pyrenebutyric acid to form a thioester.

Methods for derivatizing chelators to permit disposition onto surfaces of the FET are known in the art. For example, pyrenes are known to adsorb to carbon nanotube (CNT) surfaces through π-π interactions. By reacting a chelator, such as EGTA, with 1-pyrenebutyric acid, to form the corresponding thioester, the chelator can be adsorbed to the carbon nanotube surface. Additionally, azide chemistry has been demonstrated to be a powerful means to covalently modify carbon nanotubes. Specifically, diazonium salts react with the surface of carbon nanotube surfaces to generate C—C bonds. Through the derivatization of the chelating agent with a diazonium salt, the chelator can be attached to CNTs incorporated in the field effect transistor. In some embodiments, the diazonium salt is 4-(2,5-dioxo-2,5-dihydro-1H-pyrrol-1-yl)benzenediazonium.

5. Chelator-Coated Field Effect Transistors

In a first aspect, the disclosure provides a field-effect transistor comprising: (a) a source, (b) a drain, (c) a gate, and (d) a substrate at least partially interposed between the source and the gate, and at least partially interposed between the drain and the gate; and (2) a chelator or a derivatized chelator at least partially interposed between the source and the drain.

In some embodiments, the chelator or the derivatized chelator is at least partially interposed upon the substrate. Optionally, the chelator or the derivatized chelator is at least partially interposed between the source and the drain. In some embodiments, the chelator or the derivatized chelator is at least partially interposed upon the substrate and is at least partially interposed between the source and the drain. In some embodiments, the substrate comprises a dielectric material. Optionally, the substrate comprises Gallium Nitride.

In some embodiments, the field-effect transistor further comprises a carbon nanotube. Optionally, the carbon nanotube is at least partially interposed upon the substrate. The carbon nanotube may be at least partially interposed between the source and the drain. In some embodiments, the carbon nanotube is at least partially interposed upon the substrate and is at least partially interposed between the source and the drain.

In some embodiments, the chelator or the derivatized chelator is at least partially interposed upon the carbon nanotube. Optionally, the chelator or the derivatized chelator is at least partially interposed upon the substrate. The chelator or the derivatized chelator may be at least partially interposed between the source and the drain. Optionally, the chelator or the derivatized chelator is at least partially interposed upon the substrate and is at least partially interposed between the source and the drain.

In some embodiments, the chelator or the derivatized chelator is configured to contact a detectable label. Optionally, the detectable label comprises metal ion. The chelator or the derivatized chelator may be configured to selectively bind with the metal ion, such that the selective binding between the chelator or the derivatized chelator and the metal ion causes a change in an electrical current between the source and the drain. In some embodiments, the change in the electrical current is provided as output for use in at least one of detecting the metal ion, identifying the metal ion, or measuring an aspect of the metal ion. Optionally, a first electrical voltage is applied to the source and a second electrical voltage is applied to the drain, the first electrical voltage being different from the second electrical voltage, thereby contributing to the electrical current between the source and the drain.

Non-limiting examples of FET chips that can be used in the present disclosure are: a Gallium nitride (GaN) chip, a high quality Silicon Nanowire Field Effect Transistors (SiNW-FETs), a Metal Oxide Semiconductor Field Effect Transistor (MOSFET), a nanowire field-effect transistor (NWFET) chip, a carbon nanotube field-effect transistor (CNTFET) chip, an ion-sensitive field-effect transistor (ISFET) chip, an oxide-semiconductor field-effect transistor (OSFET) chip or a field-effect transistor chip fabricated by a complementary metal oxide semiconductor (CMOS) process. In some embodiments, the substrate comprises Gallium nitride. In some embodiments, the FETs have a semiconductor film (the channel) that is separated from an electrode (the gate) by a thin film insulator, made of e.g. silicon oxide, metal oxide or others. This gate-insulator-organic semiconductor sandwich is analogous to a capacitor that causes field-effect current modulation in the channel (between said source and drain electrodes which contact the semiconductor film). Hence the current between the source and drain electrodes can be adjusted, by tuning the voltage applied to the gate electrode.

In some embodiments, the source electrode and/or the drain electrode and/or the gate electrode comprises a material selected from the group of chromium, titanium, copper, aluminum, molybdenum, tungsten, nickel, gold, palladium, platinum, conducting polymers and oligomers, silver paste and a combination thereof. Optionally, the material is a combination of titanium and gold. In some embodiments, the material is a combination of titanium and platinum.

In some embodiments, the FET substrate comprises a dielectric material. Optionally, the dielectric material is at least partially interposed between the source and the gate, and at least partially interposed between the drain and the gate. In some embodiments, the dielectric material is a solid material, such as porcelain, glass or plastic. In some embodiments, the dielectric material is a liquid material. In some embodiments, the dielectric material is a gas, such as air, nitrogen, sulfur hexafluoride or parylene. Optionally, the dielectric material is a piezoelectric material or a ferroelectric material. Relative permittivity is typically denoted as $\varepsilon_r(\omega)$ (sometimes κ or K) and is the ratio of the capacitance of a capacitor using that material as a dielectric, compared with a similar capacitor that has vacuum as its dielectric. In some embodiments, the dielectric material has a relative permittivity higher than about 50. Non-limiting examples of dielectric materials are $SiO_2$, $Si_3N_4$, $CaCu_3Ti_4O_{12}$, $Ta_2O_5$, $TiO_2$, $SrTiO_3$, $BaTiO_3$, $Al_2O_3$ and conjugated polymers, such as $Si_3N_4/SiO_2$.

In some embodiments, the chelator or the derivatized chelator interposed between the source and the drain is configured to selectively bind the metal ion. Optionally, the binding between the chelator or the derivatized chelator and the metal ion causes a change in an electrical current between the source and the drain. In some embodiments, the change in the electrical current is provided as output for use in detecting the metal ion. Optionally, the change in the electrical current is provided as output for use in identifying the metal ion. Optionally, the change in the electrical current is provided as output for use in measuring an aspect of the metal ion.

In some embodiments, a first electrical voltage is applied to the source and a second electrical voltage is applied to the drain, the first electrical voltage being different from the second electrical voltage, thereby contributing to the change in electrical current between the source and the drain.

6. Devices Comprising Chelator-Coated Field Effect Transistors

FIG. 1. shows a schematic side cross sectional representation of a transistor device (1) and liposome immunoassay in accordance with an aspect of the present disclosure. The detection is based on the release of calcium ions ($Ca^{2+}$) (14) near the sensor-liquid-interface. The liposomes (13) containing $Ca^{2+}$ are attached to the surface of a substrate (5) (comprised of layers 30, 31, 32, 33, and 34 in the example of FIG. 1), via an immunoassay consisting of a liposome, a detection antibody (11), a target analyte (12), and capture antibody (10). A calcium chelator, such as EGTA (16), ethyleneglycol-bis(β-aminoethyl)-N,N,N',N'-tetraacetic Acid binds $Ca^{2+}$ ions near the FET gate (4). The transistor comprises a source (2) and a drain (3) deposited onto the substrate. The substrate consists of a layer of AlGaN (30), unintentionally doped (UID) GaN (31), Carbon Doped GaN (32), AlN (33) and SiC (34).

Figure 2A:
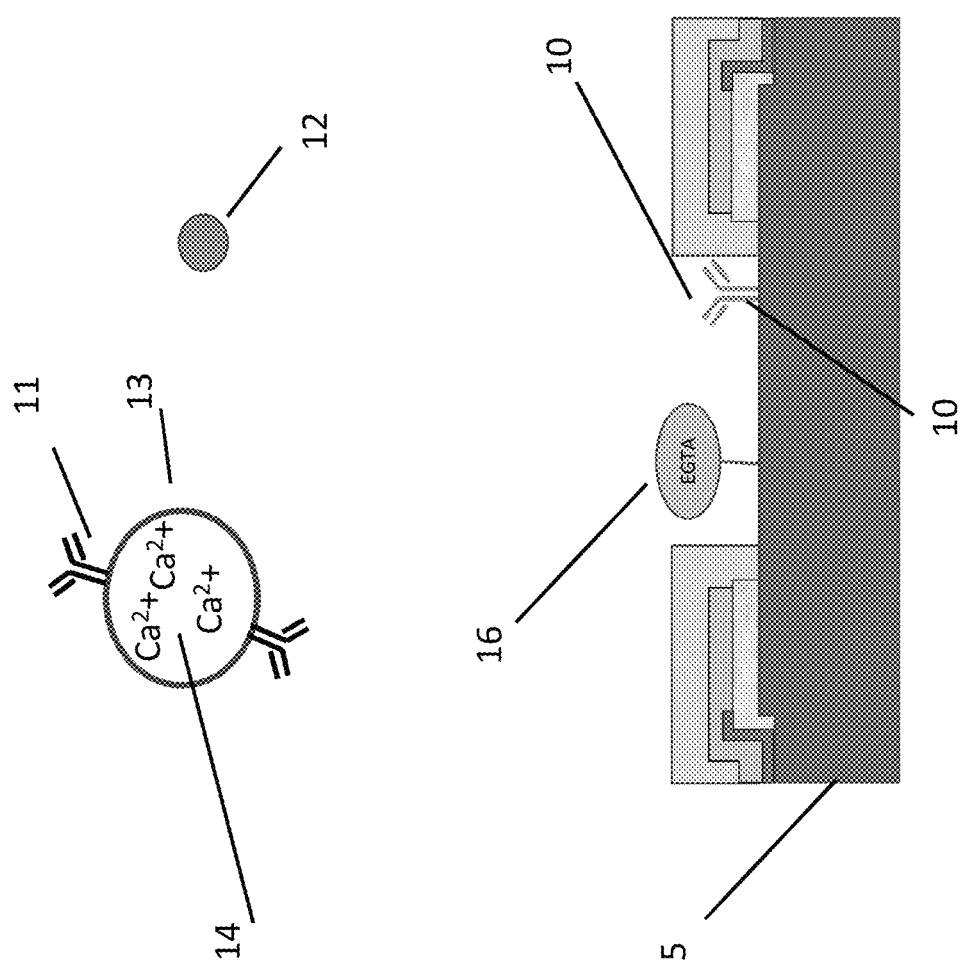
FIGS. 2 A-D show side cross sectional representations of a scheme for detection of a target analyte in solution using FETs in accordance with embodiments of the present disclosure.
Figure 2C:
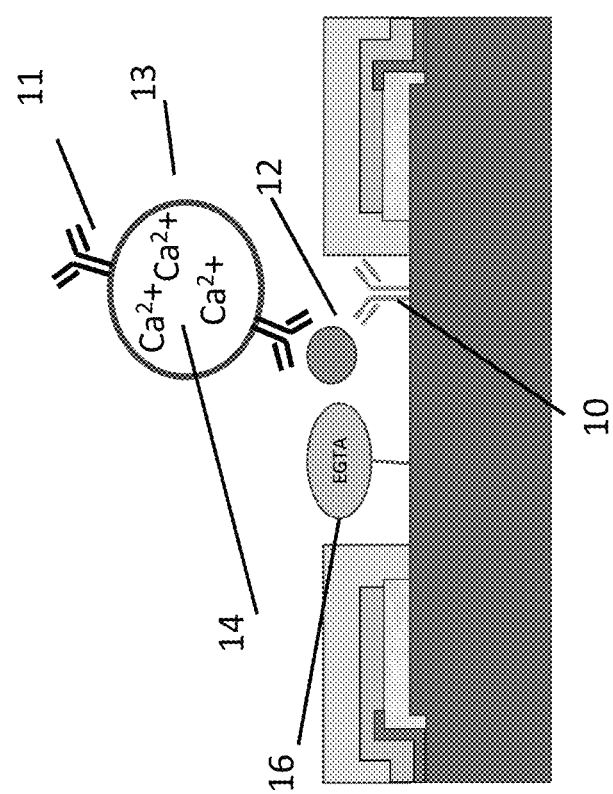
Figure 2D:
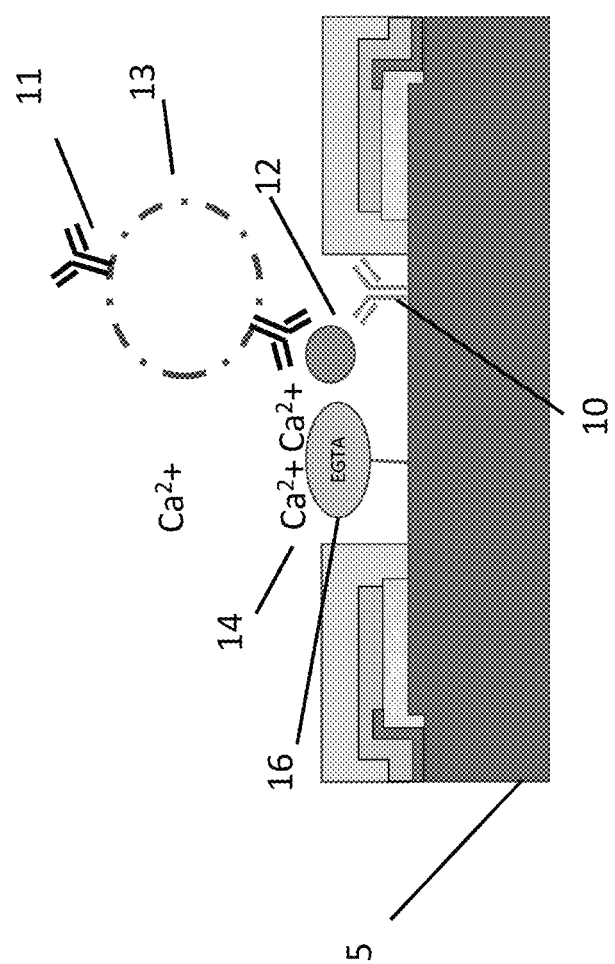

FIGS. 2A-D show side cross sectional representations of a scheme for detection of a target analyte (12) in solution using FET transistors, such as transistor (1) described herein. FIG. 2A shows liposomes (13) containing a solution of calcium ions (14) conjugated with detection antibodies (11), and target analytes (12) floating in a solution. The substrate (5) surface is functionalized with capture antibodies (10) and EGTA (16). FIG. 2B shows the liposome (13) and analyte (12) forming an immunoassay half sandwich-like structure in solution. FIG. 2C shows the formation of the immunoassay as the analyte (12) binds to the capture antibody (10) on the surface of the substrate (5). FIG. 2D shows the release of the calcium ions (14) from the liposome (13) which rapidly bind with the EGTA (16) and create a detectable voltage change in the transistor (1).

Figure 3:
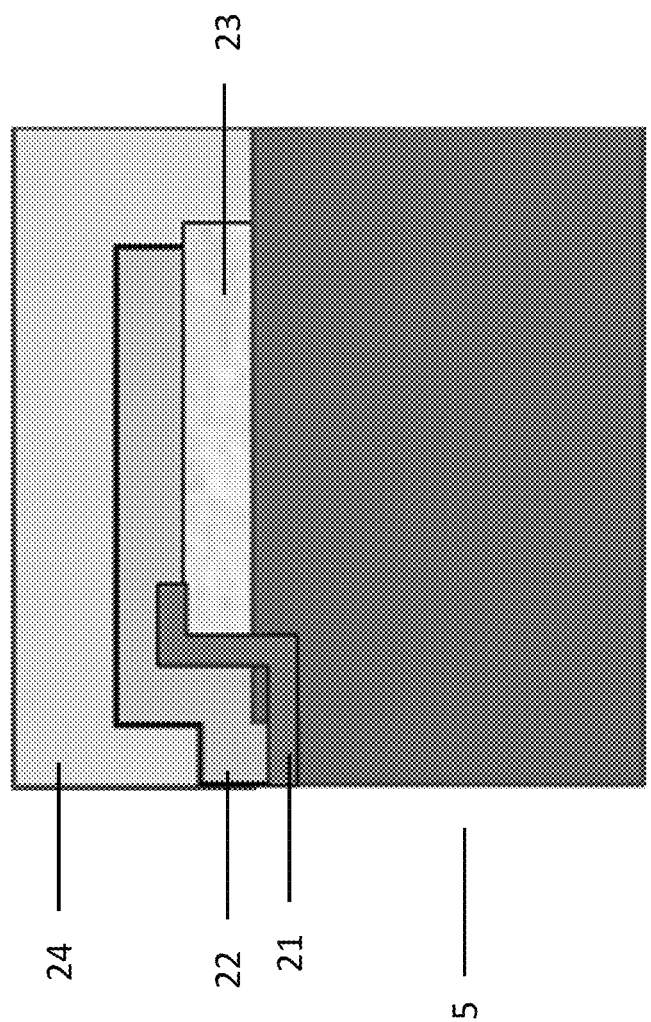
FIG. 3 shows a side cross sectional view of a lithographic deposition scheme for assembly of the FET source and drain elements, in accordance with embodiments of the present disclosure.

FIG. 3 shows a side cross sectional view of a lithographic deposition scheme for assembly of the source (2) and drain (3) elements of the FET transistor (1). The device is built on substrate (5), which may comprise GaN or AlGaN. A first layer of ohmic metallization (22) is deposited and capped on the dextral side by a layer of $SiO_2$ (21) to act as a field oxide. A gate metallization of Ti/Au or Ti/Pt (23) is deposited over the ohmic metal and is encapsulated by a layer of $SiN_3$ (24).

Figure 4:
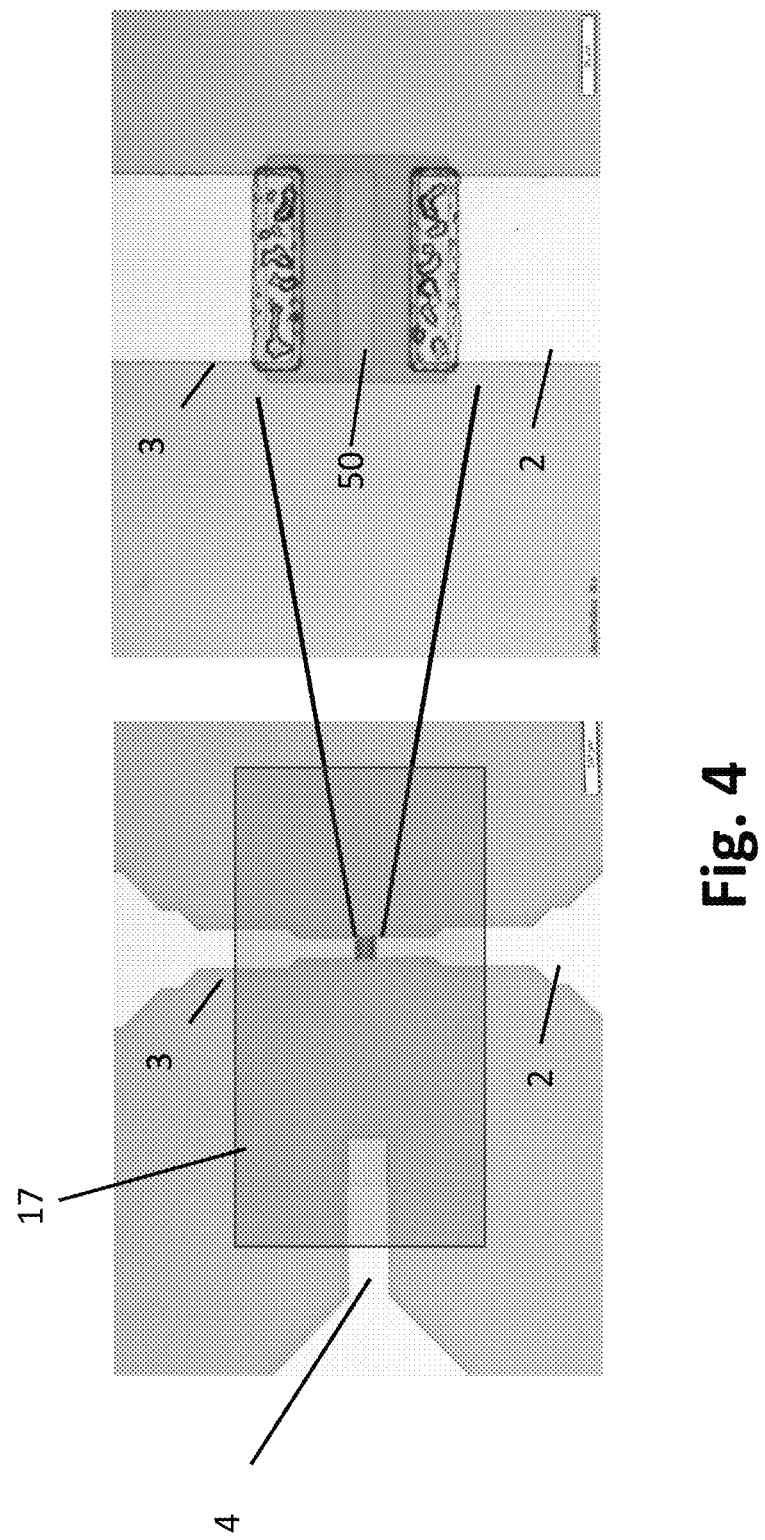
FIG. 4 shows top plan view images of FET source, drain, and gate elements with an enlarged top plan view of the bridge element at the right, in accordance with embodiments of the present disclosure.

FIG. 4 is an image of a fabricated FET transistor 1 showing the region that will be exposed to liquid (liquid region 17). FIG. 4 in particular shows top plan view images of the FET transistor source (2), drain (3), and gate (4) elements with an enlarged top plan view of a bridge element (50) at the right. A close-up image of the source drain structure shows the gate 50 region. The transistor acts as an extended gate field effect transistor (EFGET) by isolating the wet and dry environments. The sensing pads extend away from the physical transistor electronics, and only the off-chip pads are immersed into the solution. In the process of validating the embodiment of this application, a transistor was fabricated with a distance between the source-drain at ~5 μm. The FET had a source to gate distance of 5 μm, a gate width of 2 μm, and gate to drain distance of 7 μm. For the L-BioFETs, only the gate and the channel are exposed to solution. When a positive bias is applied to the gate, negative ions will accumulate on the surface of the gate electrode exposed to the buffer. At the same time, positive ions will accumulate on the surface of the channel, increasing the 2D electron gas concentration in the active channel of the L-BioFET, causing the conductivity to increase. The L-BioFET does not depend on the protein charge, rather protein binding at the gate redistributes the charge density on the gate and channel, causing a voltage drop at the gate and thus detection. The L-BioFET benefits from high ionic strength solutions since the charge re-distribution effect is enhanced.

Figure 5:
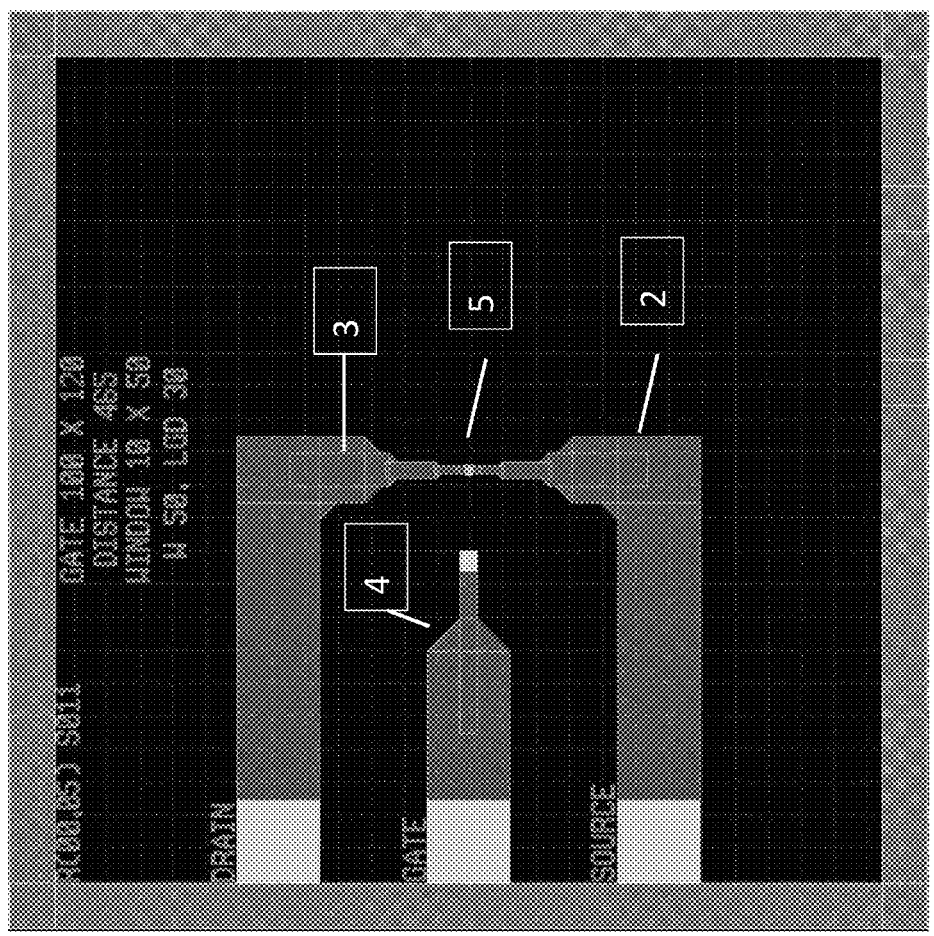
FIG. 5 shows a top plan view of a lithographic mask layout for manufacturing the FET, including gate, source, drain and bridge, in accordance with embodiments of the present disclosure.

FIG. 5 shows a top plan view of a lithographic mask layout for manufacturing the FET transistor, including gate (4), source (2), drain (3) and bridge (50). A detailed description of the scheme is found in FIG. 3.

Figure 6:
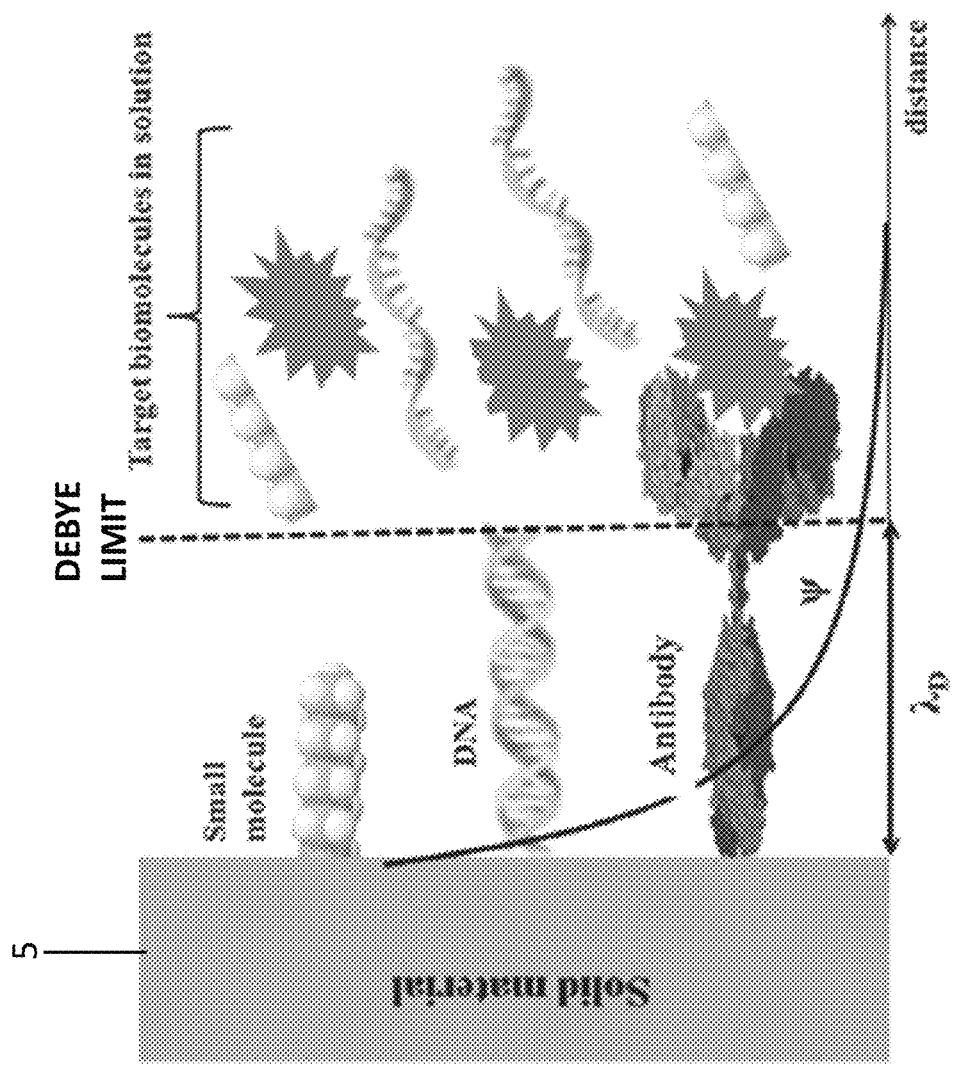
FIG. 6 shows the electrical double-layer length known as the Debye limit for materials' ability to interact with a substrate interface to make a detectable change in the device voltage, in accordance with embodiments of the present disclosure.

FIG. 6 shows the electrical double-layer length known as the Debye limit for materials ability to interact with a substrate interface 5 in order to make a detectable change in the device voltage.

Figure 7B:
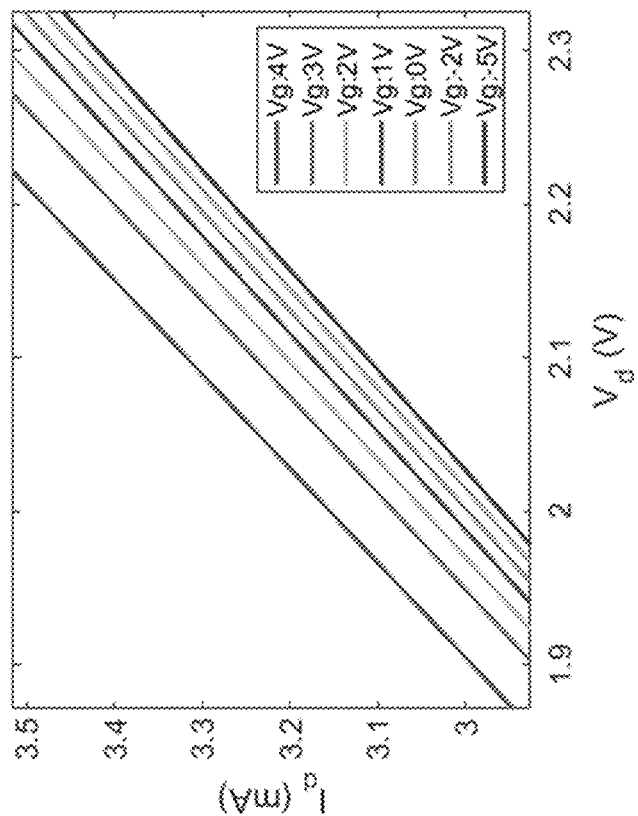
FIGS. 7A and 7B are graphs showing $I_d$ (drain current) as a function of $V_d$ (drain voltage) of measured dry $I_d$-$V_d$ curves for the FET transistor that confirms linear drain current dependence for the gate bias based on differing input voltage (−5V, −2V, 0V, 1V, 2V, 3V and 4V), in accordance with embodiments of the present disclosure, with FIG. 7B being an enlargement of the $I_d$-$V_d$ curve of FIG. 7A between 3 and 3.5 mA for the different gate voltages.
Figure 7A:
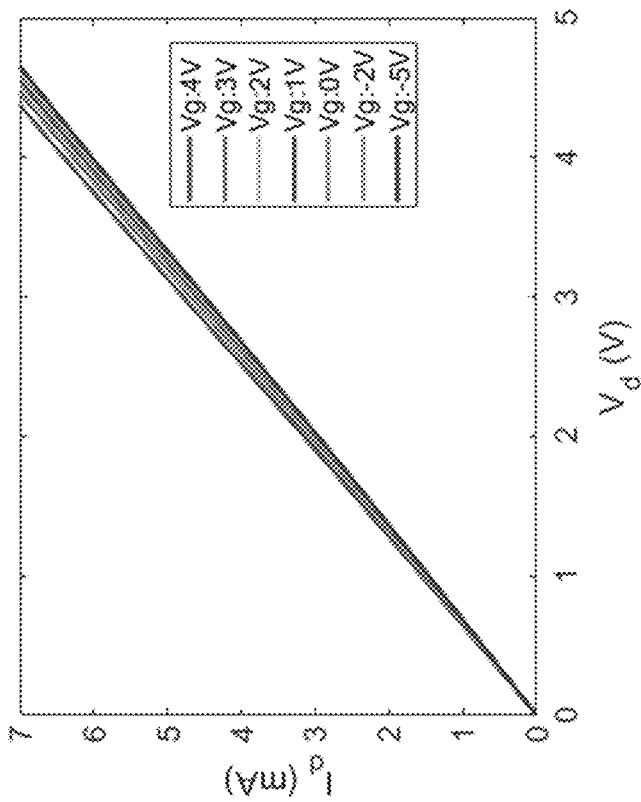

FIGS. 7A and 7B are graphs showing $I_d$ (drain current) as a function of $V_d$ (drain voltage) of the measured dry $I_d$-$V_d$ curves for the FET transistor that confirms linear drain current dependence for the gate bias based on differing input voltage (−5V, −2V, 0V, 1V, 2V, 3V and 4V). FIG. 7B is an enlargement of the $I_d$-$V_d$ curve of FIG. 7A between 3 and 3.5 mA for the different gate voltages.

Figure 8A:
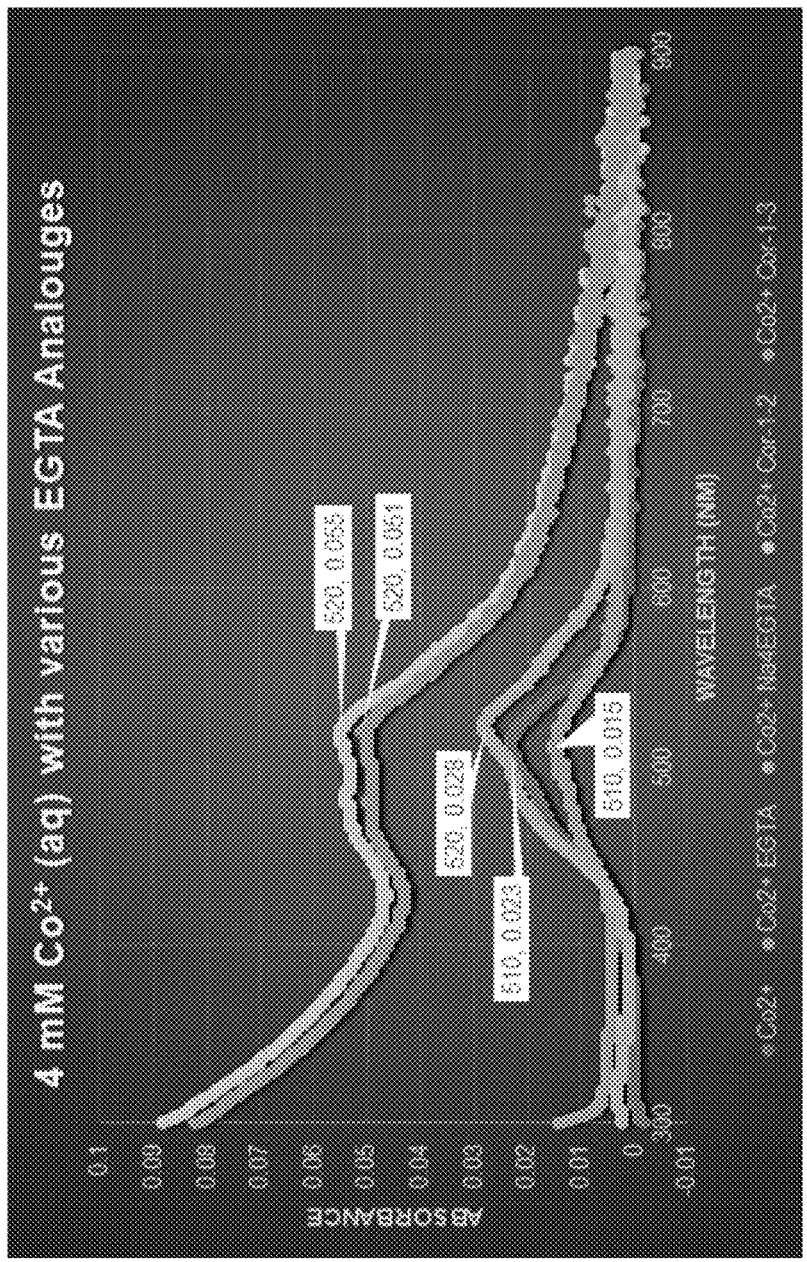
FIGS. 8A-8C show the chelation behavior of EGTA-thioacetate to $Cr^{3+}$, $Co^{2+}$ and $Cu^{2+}$ determined by measuring the absorbance at different wavelengths and comparing with protonated EGTA and other EGTA analogues in accordance with embodiments of the present disclosure.
Figure 8B:
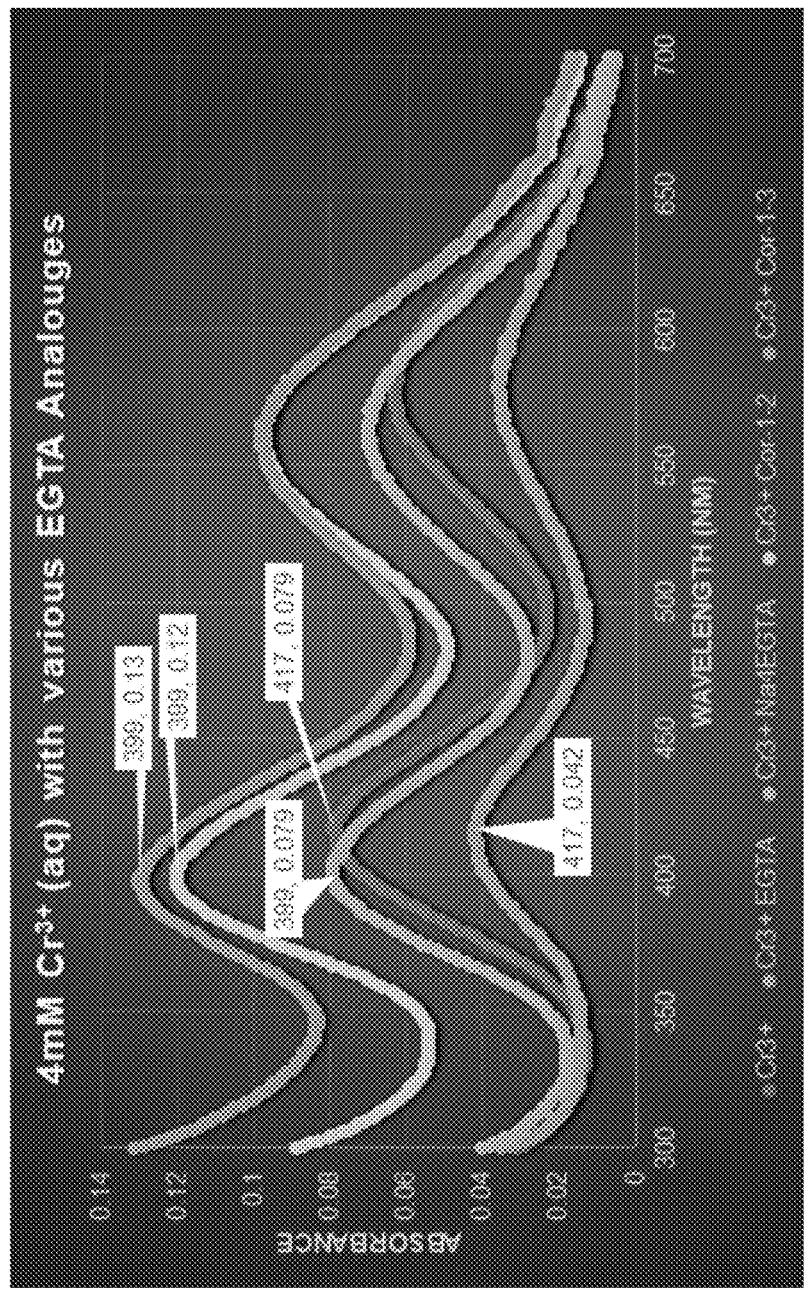
Figure 8C:
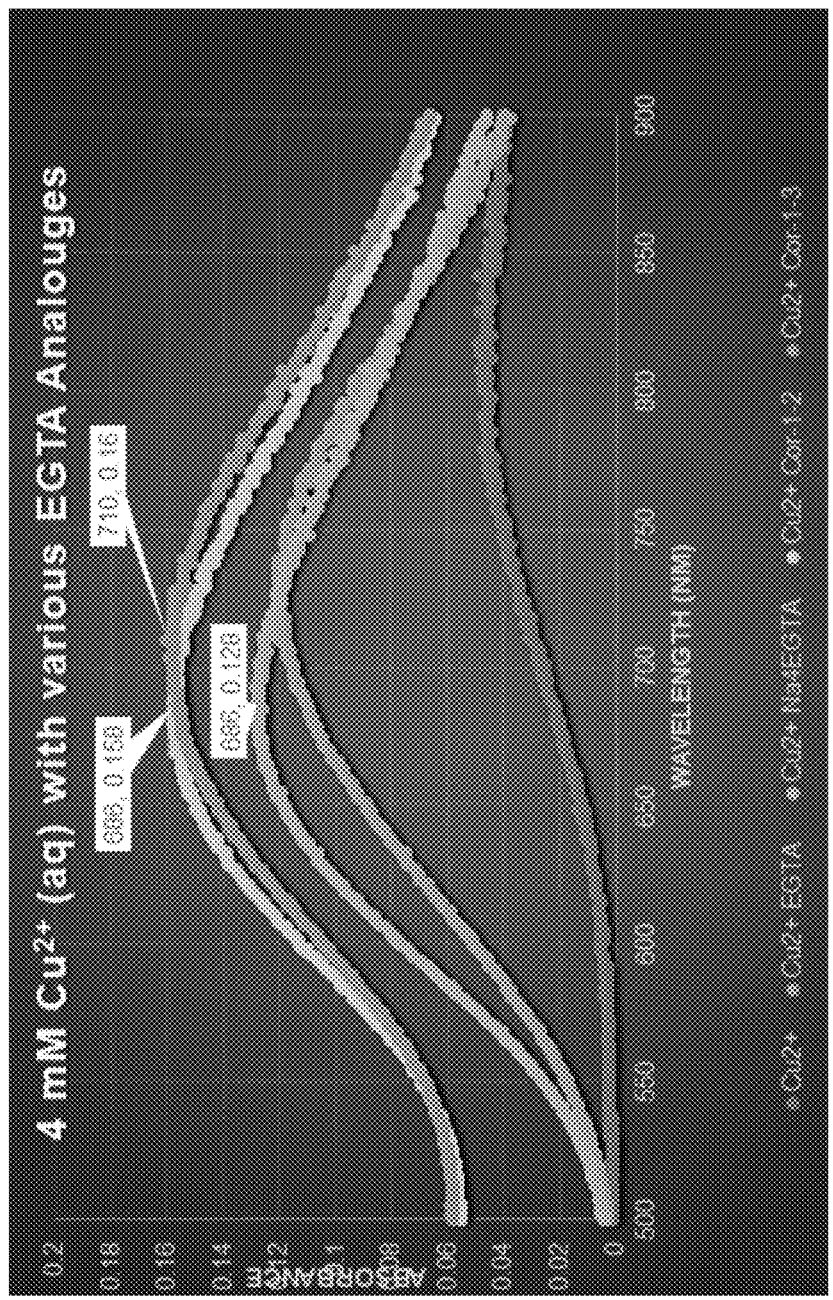

FIGS. 8A-8C. show the chelation behavior of EGTA-thioacetate to $Cr^{3+}$, $Co^{2+}$ and $Cu^{2+}$ determined by measuring the absorbance at different wavelengths and comparing with protonated EGTA and other EGTA analogues.

In a second aspect, the disclosure provides a device for sample assaying. In some embodiments, the device comprises: (1) a sensor comprising: (a) a field-effect transistor, such as the FET (1) described above and below, comprising: (i) a source (2), (ii) a drain (3), (iii) a gate (4), and (iv) a substrate (5), which may include a dielectric material, at least partially interposed between the source and the gate, and at least partially interposed between the drain (3) and the gate (4); (b) a chelator or a derivatized chelator at least partially interposed between the source (2) and the drain (3); and (2) a communication port configured to transmit sensor data based on a signal provided via at least one of the source (2) or the drain (3).

In some embodiments, the chelator or the derivatized chelator is at least partially interposed upon the substrate (5). In some embodiments, the substrate (5) comprises a dielectric material. Optionally, the chelator or the derivatized chelator is at least partially interposed between the source (2) and the drain (3). In some embodiments, the chelator or the derivatized chelator is at least partially interposed upon the substrate (5) and is at least partially interposed between the source (2) and the drain (3).

In some embodiments, the field-effect transistor (1) further comprises a carbon nanotube. Optionally, the carbon nanotube is at least partially interposed upon the substrate (5). The carbon nanotube may be at least partially interposed between the source (2) and the drain (3). Optionally, the carbon nanotube is at least partially interposed upon the substrate (5) and is at least partially interposed between the source (2) and the drain (3).

In some embodiments, the chelator or the derivatized chelator is at least partially interposed upon the carbon nanotube. The chelator or the derivatized chelator may be at least partially interposed upon the substrate (5). In some embodiments, the chelator or the derivatized chelator is at least partially interposed between the source (2) and the drain (3). Optionally, the chelator or the derivatized chelator is at least partially interposed upon the substrate (5) and is at least partially interposed between the source (2) and the drain (3).

There are several problems with conventional FETs for biological detection applications. In ionic solutions, the small ions, which carry an opposite charge to that of the detectable large macromolecule, screen the observed net charge by a cloud of opposite charge around the macromolecules. That screening is dependent on the distance between the surface ($\lambda_D$) and the point of observation (FIG. 6). At one Debye length, the charge effect on the voltage of the transistor decays 1/e, typically 1 nm. For large biomolecules such as antibodies, the area of interaction is much further out from the substrate and has very little effect on the detected voltage. For smaller DNA molecules, the interaction can occur at the boundary of the Debye limit. For small molecules, such as EGTA, the interaction falls within the Debye limit, allowing for a significant voltage shift to occur in the transistor. High ionic strength solutions pose difficulties for C-BioFETs since they are sensitive to protein charge and require a reference electrode. In a C-BioFET, the detection mechanism is based on the charge or potential of the target protein, which results in a potential change near the surface of the channel, thus causing a current change. This mechanism is constrained by the Debye length and the high ionic strength of the buffer required to maintain the conformation of the protein or biological sample. The signal amplifications described herein help overcome this limitation allowing a C-BioFET to deliver more charges to the channel.

In some embodiments, the substrate of the field-effect transistor comprises GaN (Gallium nitride). GaN is a high electron mobility transistor (HEMT) with a higher critical electric field strength than silicon which means that a GaN device can have a smaller size for a given on-resistance and breakdown voltage than silicon. GaN also offers extremely fast switching speed and excellent reverse-recovery performance, critical for low-loss, high-efficiency performance. In some embodiments, the GaN FET chip, the source and drain electrodes pierce through the top AlGaN layer to form an ohmic contact with the underlying 2DEG (two-Dimensional Electron Gas). Layers of GaN, carbon doped GaN and AlN are placed underneath the AlGaN layer. In some embodiments, the field-effect transistor is a MOSFET (Metal Oxide Semiconductor Field Effect Transistor or Metal Oxide Silicon Transistor).

In some embodiments, the FET comprises a p-channel (pFET). In other embodiments, the FET comprises a n-channel (nFET).

Depending on the type of FET (pFET or nFET), two different situations arise. In some embodiments, the voltage applied between the gate and the substrate ("$V_G$") generates an electric field through the oxide layer, creating an inversion channel under the gate oxide. In other embodiments, in the case of a pFET transistor, the n-type substrate is inverted to p-type in a thin layer under the gate oxide, and a p-type substrate is similarly inverted to n-type in an nFET device. Because the inversion channel is of the same type as the source and drain, current can now pass from source to drain.

By varying the potential between the gate and substrate, the inversion channel in which current flows can be altered to control the magnitude of the current or be turned off completely. Thus, the magnitude of the drain source current, "$I_D$", through the channel is controlled by the potential difference $V_G$ applied between the source S and the gate G. The threshold voltage, "$V_T$", is the value of $V_G$ where the drain current just begins to flow. Typical values range from 0.3 to 0.8 V.

The dependence of drain current ($I_D$) on the voltage between drain and source ("$V_D$") varies for different values of $V_G$. At low $V_D$, the drain current increases almost linearly with $V_D$, resulting in a series of straight lines with slopes increasing with $V_G$. At high $V_D$, the drain current saturates and becomes independent of $V_D$.

Without being bound by theory, the following paragraphs describe the functioning of the FETs, such as FET (1) described above, of the present disclosure. In some embodiments, to make an n-channel FET, donors are diffused in the source (2), drain (3) regions (forming n-regions) in a p-type substrate (5), and grow an oxide layer that acts as the gate oxide. With a small positive voltage on the drain (3) and no bias on the gate, i.e., $V_D>0$ and $V_G=0$, the drain is a reverse-biased p-n junction. Conduction band electrons in the source (2) region encounter a potential barrier determined by the built-in potential of the source junction. As a result, no electrons enter the channel region, and hence no current flows from the source to the drain. This is referred to as the "off" state.

With a small positive bias on the gate, band bending in the channel region (surface potential $\psi_s>0$) brings the conduction band in the channel region closer to the conduction band in the source region, reducing the height of the potential barrier to electrons. At a critical value of $V_G$, termed the "threshold voltage" ("$V_T$"), an inversion layer is created. The inversion layer supports current flow from drain D to source S, and electrons can now enter the channel and flow from source to drain. This is referred to as the transistor being in an "on" state. In the low drain bias regime, the drain current increases almost linearly with drain bias, and like an ideal resistor it obeys Ohm's law.

The channel resistance is determined by the electron concentration in the channel, which is a function of the gate bias. As the gate bias is increased, the slopes of the linear portion of the I-V characteristics in FIG. 7A gradually increased as a result of the increasing conductivity of the channel. The drain current $I_D$ is given by:

$$I_D = \frac{1}{2}\mu_e C_{ox} \frac{W}{L}\left[2(V_G - V_T)V_D - V_D^2\right]$$

This is the expression needed to compare a Si-FET and a GaN-FET, wherein the dimensions are width (W) and length (L); $V_G$, $V_T$, $V_D$ are the gate, threshold and drain voltages, respectively; e is the effective channel mobility of the electrons and $C_{ox}$ is the capacitance of the gate dielectric. For small $V_D$ ($V_D \ll V_G-V_T$), the second term $V_D$ can be ignored, and the expression for the drain current reduces to a straight line with a slope $$\left(\frac{\partial}{\partial}\frac{I_D}{V_D}\right)$$

equal to the gain factor (g) of the device.

In an idealized MOS capacitor, without any applied voltage, the metal work function, $\varphi_m$, is equal to the semiconductor work function, $\varphi_s$. Therefore, the Fermi level of the semiconductor, EFS, is aligned with the Fermi level of the gate, $E_{Fm}$. As a consequence, there is no band bending in any region of the MOS capacitor. It is also assumed here that the oxide is free of any charges, and the semiconductor is uniformly doped. The condition, where the majority carrier concentration is greater near the Si—SiO$_2$ interface compared with the bulk concentration, is called "accumulation". Under this applied negative gate bias, the Fermi level of the gate is raised with respect to the Fermi level of the substrate by an amount $qV_G$. The energy bands in the p-type semiconductor are bent upward, bringing the valence band closer to the Fermi level, which is indicative of a higher hole concentration at the semiconductor surface right under the dielectric. Because no current flows through the device due to the presence of the insulating oxide layer, the Fermi level in the substrate (the semiconductor) remains invariant even with an applied bias.

The applied gate voltage ($V_G$) divides between the gate dielectric and the semiconductor such that:

$$V_{GB}=V_{ox}+V_s \quad (2)$$

where $V_{GB}$ is the gate bias, $V_{ox}$ and $V_s$ are the voltages that drop across the oxide and the semiconductor, respectively. The bands in the oxide drop linearly over the bulk of the oxide thickness an amount equal to $qV_{ox}$, and the electric field in the oxide can be expressed as:

$$E_{ox} = \frac{V_{ox}}{t_{ox}} \quad (3)$$

where $t_{ox}$ is the oxide (dielectric) thickness. The amount of band bending in the semiconductor is principally located at the surface and is equal to $q\psi_\sigma$, where $\psi_s$ is the surface potential and is negative when the band bend is upward. When applying a positive gate bias $V_{GB}$ to counterbalance the positive gate charge, the holes under the gate are pushed away, leaving behind ionized, negatively charged acceptor atoms ($N_{A-}$), which create a depletion region. The charge in the depletion region of width W and area A is exactly equal to the charge on the gate to preserve charge neutrality [$Q_G(+)=Q_c(-)=-qN_A-AW$]. With a positive gate bias, the Fermi level of the gate is now lowered with respect to the Fermi level of the semiconductor. The bands bend downward, resulting in a positive surface potential. Under the gate, the valence band moves away from the Fermi level, which is indicative of hole depletion. When the band bending at the surface is such that the intrinsic level ($E_i$) coincides with the doped semiconductor Fermi level ($E_{FS}$), the surface region resembles an intrinsic material. The surface potential for this condition is given by:

$$\psi_s = \phi_F = \frac{1}{q}(E_i - E_F) \quad (4)$$

where $\phi_F$, the Fermi potential, is given by:

$$\phi_F = \frac{kT}{q}\ln\frac{N_A}{n_i} \quad (5)$$

where $n_i$ is the charge carrier density of the intrinsic material (typically $n_i \approx 1.5 \times 10^{10}$ cm$^{-3}$ at 300 K in pure Si). Applying a larger positive gate bias, the positive charge on the gate increases further, and thermally generated electrons start collecting under the gate. With these electrons, the intrinsic surface region begins to convert into an n-type inversion layer. The negative charge in the semiconductor is now composed of both ionized acceptor atoms in the depletion layer and free electrons in the inversion layer. In this condition, the electron concentration at the surface is still less than the hole concentration in the neutral bulk of the semiconductor, and this regime is called weak inversion. The point where the surface potential $\psi_s$ equals the Fermi potential $\phi_F$ is defined as the onset of weak inversion. As the gate bias is further increased, the band bending also continues to increase. This causes the depletion region to become wider while the electron concentration in the inversion layer increases more and more. At the gate bias where the electron concentration in the inversion region is equal to the hole concentration in the bulk, a strong inversion layer is created. The surface potential to achieve this strong inversion is given by:

$$\psi_s = 2\phi_F = \frac{2}{q}(E_i - E_F) \quad (6)$$

When the gate bias is increased beyond this value, new electrons in the inversion layer readily compensate extra positive charge on the gate and the depletion layer width does not further increase, and hence the band bending increases only very slightly. The maximum depletion layer width, $W_d$, at the onset of strong inversion is then given by:

$$W_d = \sqrt{\frac{4\phi_F \varepsilon_s}{qN_A}} \quad (7)$$

where $\varepsilon_s = 1.053 \times 10^{-10}$ F/m is the permittivity of silicon. In a real MOS device, the work function of the metal, $\varphi_m$, is not likely to be equal to that of the semiconductor, $\varphi_s$. For a MOS capacitor with $\varphi_m < \varphi_s$ at zero gate bias, electrons in the metal reside at energy levels above the conduction band of the semiconductor. Thus, electrons will flow from the metal into the semiconductor until a potential counter balances the difference in the work functions between the two plates of the MOS capacitor. This induces a negative charge under the gate dielectric, accompanied by a downward band bending and hence a preexisting positive surface potential $\psi_{ms}$. With an external voltage, equal to this difference $\psi_{ms}$, applied to the gate, the net charge in the semiconductor disappears, and the bands return to their flat position. This applied voltage is defined as the flat band voltage, "VFB", and is expressed as:

$$V_{FB} = q\psi_{ms} = q(\varnothing_m - \varnothing_s) \quad (8)$$

The oxide and the semiconductor/oxide interface are not perfect, and another modification to the ideal picture of a MOS capacitor comes from charges that reside in the dielectric or at its interface. Such charges originate from processing, defects in the bulk, or charges that exist at the interface between Si and SiO$_2$. Charges in the bulk oxide, or at the interface, induce opposite charges in the semiconductor and the gate. This again causes the bands to bend up or down, and the flatband voltage has to be adjusted to take this into account. The flatband voltage can then be expressed as:

$$V_{FB} = q\phi_{m,s} - \frac{Q_o}{C_{ox}} \quad (9)$$

where $Q_o$ is the oxide charge, and $C_{ox}$ is the oxide capacitance. Defects located at the Si/SiO$_2$ interface may not be fixed in their charged state, and the amount of charges may also vary with the surface potential of the semiconductor. These defects are referred to as "fast interface traps", and they impact the switching characteristics of FETs. A MOS capacitor is then placed between a source (S) and a drain (D).

When the semiconductor (body) is at ground potential ($V_B=0$), the threshold voltage, $V_T$, equals the sum of the flatband voltage $V_{FB}$, the voltage across the oxide due to the depletion layer charge ($Q_d=-qN_A-W_d$) with $W_d$ given by Equation 1-7, and twice the bulk potential ($\psi_s=2\phi_F$) or:

$$V_T = q\phi_{m,s} - \frac{Q_o}{C_{ox}} - \frac{Q_d}{C_{ox}} + 2\phi_F (nMOSFET) \quad (10)$$

$$V_T = q\phi_{m,s} - \frac{Q_o}{C_{ox}} - \frac{Q_d}{C_{ox}} + 2\phi_F (pMOSFET) \quad (11)$$

where $$Q_d(nMOSFET) = -2\sqrt{qN_A\phi_F\varepsilon_s} \text{ and } Q_d(pMOSFET) = 2\sqrt{qN_D\phi_F\varepsilon_s} \quad (12)$$

Finally, we come back to Equation (1):

$$I_D = \frac{1}{2}\mu_e C_{ox}\frac{W}{L}[2(V_{GS} - V_T)V_{DS} - V_{DS}^2] \quad (13)$$

Control of the threshold voltage is crucial in making FETs. In some embodiments, highly doped polysilicon can be used as the gate material. In other embodiments, Aluminum can be used as the gate material. By using highly doped polysilicon as the gate material instead of Al, $\varphi_{m,s}$ is now just the difference in Fermi levels of the two silicon regions. Polysilicon is also more process friendly as it can withstand higher temperatures than Al. In Equation 1, the gate oxide capacitance $C_{ox}$ (F/m$^2$) is given by: $\varepsilon_{ox}/t_{ox}$ with $\varepsilon_{ox}=3.5\times 10^{-11}$ F/m) and where $t_{ox}$ is the oxide thickness. A larger $C_{ox}$ leads to a smaller threshold. In a 0.24-µm FET process, $t_{ox}$ is 5 nm (~10 atom layers), and $C_{ox}$ is 5.6 fF/µm$^2$. With even thinner oxide films, about 2 nm, large tunneling currents lead to leakage and high power consumption. In some embodiments, the dielectrics used for the gate have a higher dielectric constant cox, such as for example, $ZrO_2$, $HfO_2$, and $Al_2O_3$.

Solid State GaN FET Transistor

In some embodiments, the FET transistor is based on GaN (Gallium nitride).

For small $V_D$, the second term in parentheses in Equation (1) above can be ignored, and the expression for drain current then reduces to:

$$I_D = \mu_e C_{ox}\frac{W}{L}[(V_{GS} - V_T)V_{DS}] \quad (14)$$

which is a straight line with a slope equal $(dI_D/dV_D)$ to the gain factor, g, of the device:

$$g = \mu_e C_{ox}\frac{W}{L} \quad (15)$$

and $\mu_e C_{ox}$ is the device's transconductance g. For larger drain biases, the drain current saturates and becomes independent of the drain bias. This region is referred to as the "saturation region". The drain current saturation is derived again from Equation 1, which is parabolic with a maximum occurring at $|V_{D, max}|=|V_G-V_T|$, where $V_{DS, max}$ is also called the "pinch-off voltage". To calculate the drain current, $I_D$, in this saturation region we substitute $|V_{DS, max}|=|V_G-V_T|$ in Equation (1) to obtain:

$$I_D = \mu_e C_{ox}\frac{W}{L}V_{D,max}^2 \quad (16)$$

When $|V_{DS, max}|=|V_G-V_T|$, the channel is flowing as much current as it can, and the inversion layer now starts changing shape and it is eventually pinched off.

In the case of a GaN FET, Equation (15) is rewritten as:

$$g = \mu_e C_I \frac{W}{L} \quad (17)$$

where $$C_i = \left(\frac{\varepsilon \cdot \varepsilon_0}{z}\right)$$

is the capacitance per unit area between the electrolyte and the 2DEG channel, and $\mu_e$ is the electron mobility. Keeping (W/L) and $V_d$ aside, µ/z is the primary parameter to obtain a high transconductance value and therefore, high transduction sensitivity. A thin barrier (lower z) and keeping a high mobility value is key for a GaN BioFET. The shrinkage of the barrier has the effect to increase the transconductance of the device, and this makes the 2-dimensional electron density (2DEG) at the interface very sensitive to changes in the surface. The maximum velocity of charge carriers in GaN in the presence of very high electric fields is the largest for GaN. The peak velocity for GaN is close to $3\times 10^7$ cm/s and the saturation velocity about $2.6\times 10^7$ cm/s.

GaN also has the highest Critical Field $E_{crit}$, which is related to the semiconductor breakdown voltage, $V_{br}$ as:

$$V_{br} = \frac{\varepsilon_{Semiconductor} E_C^2}{2q N_d} \quad (18)$$

Exploitation of the chemical stability of GaN is also beneficial due to the challenging requirements for measurement in liquid environments while the optically transparent nature of these structures when grown on sapphire substrates is additionally very advantageous for biological applications where simultaneous monitoring of electronic and microscopic processes is critical. So, in terms of using GaN for a FET, the novel applications become apparent. Due to the strong electronegativity of nitrogen, dipole moments are induced along the Ga—N as well as the Al—N bonds. But Al and Ga possess different electronegativities, leading to a change in the macroscopic polarization at the AlGaN/GaN interface. From electrostatics a polarization P is equivalent to a surface charge a with opposite sign at the two interfaces perpendicular to the vector P. This results in a negative surface charge −σ at the surface of the AlGaN, and a positive surface charge +σ at the AlGaN/GaN interface. Additionally, GaN is a biocompatible material. In some embodiments, GaN is used for the manufacturing of the FET.

In some embodiments, the device further comprises a sample portion that can receive a sample comprising a marker and can place the marker in contact with the FET. Optionally, the marker contacts a capture antibody specific for the marker that is interposed on the FET. In some embodiments, the marker is a biomarker, an environmental marker, an allergen, or a microorganism. In some embodiments, the sample is an environmental sample, a food sample, or a sample obtained from a subject.

Optionally, the device further comprises a detectable label and means for placing the detectable label in contact with the chelator or the derivatized chelator. Optionally, the detectable label comprises a metal ion. In some embodiments, the chelator or the derivatized chelator is configured to complex with the metal ion, such that the formation of a complex between the chelator or the derivatized chelator and the metal ion causes a change in an electrical current between the source and the drain. Optionally, the change in the electrical current is provided as output for use in at least one of detecting the metal ion, identifying the metal ion, or measuring an aspect of the metal ion. In some embodiments, a first electrical voltage is applied to the source and a second electrical voltage is applied to the drain, the first electrical voltage being different from the second electrical voltage, thereby contributing to the electrical current between the source and the drain.

In some embodiments, the device further comprises a signal processor, wherein the signal processor is coupled to the communication module and is coupled to at least one of the source or the drain, and wherein the signal processor is configured to subject the signal to one or more signal processing algorithms, including at least one of an algorithm for detecting the metal ion, an algorithm for identifying the metal ion, or an algorithm measuring an aspect of the metal ion. Optionally, the signal processor generates an output based on the one or more signal processing algorithms and provides the output as the sensor data via the communication port.

In some embodiments, the device is a microfluidics device.

In some embodiments, the device further comprises means for removing the detection molecule (e.g. detection antibody or detection antibody conjugate) not bound to the marker. In some embodiments, the device comprises means for washing or filtering the detection molecule-bound (e.g. detection antibody-bound) marker. Optionally, the device comprises means for contacting the detection antibody-bound marker with a wash buffer. Preferably, the wash buffer is non-ionic.

7. Methods of Detecting a Metal Ion

In a third aspect, the present disclosure provides a method for detecting a metal ion. In some embodiments, the method uses a field-effect transistor (1) comprising a source (2), a drain (3), a gate (4), and a substrate (5), the substrate (5) being at least partially interposed between the source (2) and the gate (4), and being at least partially interposed between the drain (3) and the gate (4); and a chelator or a derivatized chelator being at least partially interposed between the source (2) and the drain (3), the method comprising:
(1) contacting the FET (1) with a detectable label comprising a metal ion, thereby placing the detectable label in contact with the chelator or the derivatized chelator;
(2) selectively binding the metal ion to the chelator or the derivatized chelator thereby causing a change in an electrical current between the source and the drain; and
(3) generating an output representing the change in the electrical current for use in at least one of detecting the metal ion, identifying the metal ion, or measuring an aspect of the metal ion.

In some embodiments, the field-effect transistor is any of the field-effect transistors disclosed herein. In some embodiments, the sensor is any of the sensors disclosed herein. Optionally, the method is performed on any of the devices disclosed herein.

8. Sensors and Methods for Detection of Markers

In a fourth aspect, the present disclosure provides a sensor for the detection of markers. In some embodiments, the sensor comprises a liposome in solution containing a metal ion, the liposome including a detection antibody configured to bind a target marker; the sensor comprising:
(a) a field-effect transistor with a source-drain channel functionalized with a capture antibody to selectively bind to the target marker; and
(b) a metal ion chelator or metal ion derivatized chelator in the source-drain channel, which metal ion chelator or metal ion derivatized chelator selectively binds with the metal ion in the liposome to cause a change in current in the field-effect transistor.

In a fifth aspect, the present disclosure provides a method for the detection of a marker. In some embodiments, the method comprises:
providing a liposome in solution containing a metal ion, the liposome including a detection antibody configured to bind a target marker; and
providing a field-effect transistor with a source-drain channel functionalized with a capture antibody to selectively bind to the target marker;
providing a metal ion chelator or metal ion derivatized chelator in the source-drain channel;
selectively binding the metal ion chelator or metal ion derivatized chelator with the metal ion in the liposome; and
causing a change in current in the field-effect transistor as a result of the selective binding the metal ion chelator or metal ion derivatized chelator with the metal ion in the liposome; and
wherein the detection of the metal ions is indicative of detection of the marker.

In a sixth aspect, the present disclosure provides an improved selective, sensitive and robust method for the detection of a marker. In some embodiments, the method uses a chelator-coated field effect transistor defined on a transistor substrate and having a source-drain channel functionalized with a capture antibody to selectively bind to the marker, the field effect transistor characterized by a conductivity and gain (beta). Optionally, the method comprises:
disposing a metal ion chelator or metal ion derivatized chelator in the source-drain channel;
disposing a liposome containing a metal ion into the source-drain channel of the field effect transistor, the liposome including a detection antibody configured to selectively bind the marker;
disrupting the liposome to release at least some of the metal ion within the liposome into the source-drain channel of the field effect transistor;
selectively conjugating the metal ion chelator or metal ion derivatized chelator with the metal ion in the liposome to immobilize the marker on the transistor substrate; and
washing the source-drain channel of the field effect transistor;
detecting an amplified detectable current in the field-effect transistor as a result of the selective conjugation of the metal ion chelator or metal ion derivatized chelator with the metal ion in the liposome by changing the conductivity of the field effect transistor and thereby changing the gain (beta) of the field effect transistor, whereby detection of metal ions indicative of detection of the marker is achieved.

Optionally, the metal ion chelator or metal ion derivatized chelator selectively binds the metal ion. In some embodiments, the selective binding of the metal ion chelator or metal ion derivatized chelator with the metal ion in the liposome occurs without substantial interference of the detection of the metal ion by screening by oppositely charged ions and unrelated ions in the solution. In some embodiments, the binding of metal ions in the sensor or method occurs on the order of $10^8$-$10^{12}$ events per second without substantial interference of the detection of the metal ions by screening by oppositely charged ions and unrelated ions in the solution. In some embodiments, the small ions, which carry an opposite charge to that of the detectable marker, screen the observed net charge by a cloud of opposite charge around the marker. The sensor according to the disclosure overcomes this problem, because the interference is minimized. Optionally, the binding of metal ions in the sensor occurs on the order of $10^{10}$ events per second without substantial interference of the detection of the metal ions by screening by oppositely charged ions and unrelated ions in the solution.

In some embodiments, the source-drain channel or the substrate of the FET comprises Gallium Nitride. In some embodiments, the source and/or the drain comprises a material selected from the group of chromium, titanium, copper, aluminum, molybdenum, tungsten, nickel, gold, palladium, platinum, conducting polymers and oligomers, silver paste and a combination thereof. In some embodiments, the source and/or the drain comprises a combination of titanium and platinum. In some embodiments, the source and/or the drain comprises a combination of titanium and gold.

In some embodiments, the field-effect transistor of the sensor or method further comprises a carbon nanotube. In some embodiments, the carbon nanotube is at least partially interposed between the source and the drain. In some embodiments, the chelator or the derivatized chelator is at least partially interposed upon the carbon nanotube.

The amplification approach of the marker is based on the rapid release of metal ions near the sensor-liquid-interface. The capture antibody may be conjugated to the substrate surface of the FET. Optionally, the chelator or derivatized chelator is conjugated to the surface of the FET. Preferably, the capture antibody and the chelator or derivatized chelator are conjugated to the substrate surface of the FET device.

In a second step, the detection antibody, linked to liposomes containing the metal ions (e.g. calcium ions), selectively recognizes the target marker, and the conjugate liposomes-antibody-marker are put into contact with the capture antibody conjugated to the substrate surface. Alternatively, the capture antibody conjugated to the substrate surface selectively recognizes the target marker, and the detection antibody, linked to liposomes containing the metal ions (e.g. calcium ions) is put into contact with the capture antibody-bound marker.

In some embodiments, a wash step is performed to remove the free liposomes conjugated detection antibodies, not specifically bound to the capture antibody-bound (i.e. immobilized) marker.

In some embodiments, a detergent is used to destabilize and disrupt the phospholipid bilayers of liposomes, so that the release of the calcium ions occurs.

To bring metal ions near the surface of the channel or gate, the chelator or derivatized chelator may be conjugated to the substrate surface and binds metal ions near the FET gate.

If the marker has bound to the detection antibody and the capture antibody and metal ions have been released upon disruption of the liposomes, this results in a detectable voltage shift associated with the change in current across the transistor due to the binding of metal ions to the chelator or derivatized chelator at the substrate surface, changing the transistor's electronic characteristics.

The change in current is measured using cyclic voltammetry, specifically, a potentiostat.

In some embodiments, the sensor or method selectively detects a marker by detecting the ions released from the liposomes. In any of the FETs, sensors, devices, or methods disclosed herein, the metal ion being detected is, optionally, selected from the group consisting of $Ca^{2+}$, $Fe^{2+}$, $Fe^{3+}$, $Mg^{2+}$, $Mn^{2+}$, $Cu^{2+}$, $Cu^{3+}$, $Zn^{2+}$, $Ni^{2+}$, $Co^{2+}$ and a heavy metal ion (e.g., $As^{+3}$, $Hg^{+2}$, $Sb^{+3}$, and $Au^+$). Preferably, the metal ions to be detected are divalent and trivalent ions.

In some embodiments, chelating agents of metallic ions include chelating agents of $Ca^{2+}$, $Fe^{2+}$, $Fe^{3+}$, $Mg^{2+}$, $Mn^{2+}$, $Cu^{2+}$, $Cu^{3+}$, $Zn^{2+}$, $Ni^{2+}$, $Co^{2+}$, heavy metal ions (e.g., $As^{+3}$, $Hg^{+2}$, $Sb^{+3}$, and $Au^+$), and the like.

In some embodiments, the chelating agent or derivatized chelating agent selectively binds a metal ion. Optionally, the chelating agent or derivatized chelating agent binds several metal ions. The chelating agent or derivatized chelating agent may preferentially bind one metal ion, but still bind other metal ions. In some embodiments, the chelator is a custom designed chelator.

In some embodiments, the chelator is selected from the group consisting of 1,1,1-Trifluoroacetylacetone; 1,4,7-Trimethyl-1,4,7-triazacyclononane; 2,2'-Bipyrimidine; Acetylacetone; Alizarin; Amidoxime; Amidoxime group; Aminoethylethanolamine; Aminomethylphosphonic acid; Aminopolycarboxylic acid; ATMP; BAPTA; Bathocuproine; BDTH2; Benzotriazole; Bidentate; Bipyridine; 2,2'-Bipyridine; Bis(dicyclohexylphosphino)ethane; 1,2-Bis(dimethylarsino)benzene; 1,2-Bis(dimethylphosphino)ethane; 1,2-Bis(diphenylphosphino)ethane; Calixarene; Carcerand; Catechol; Cavitand; Chelating resin; Chelex 100; Citrate; Citric acid; Clathrochelate; Corrole; Cryptand; 2.2.2-Cryptand; Cyclam; Cyclen; Cyclodextrin; Deferasirox; Deferiprone; Deferoxamine; Denticity; Dexrazoxane; Diacetyl monoxime; Trans-1,2-Diaminocyclohexane; 1,2-Diaminopropane; 1,5-Diaza-3,7-diphosphacyclooctanes; 1,4-Diazacycloheptane; Dibenzoylmethane; Diethylenetriamine; Diglyme; 2,3-Dihydroxybenzoic acid; Dimercaprol; 2,3-Dimercapto-1-propanesulfonic acid; Dimercaptosuccinic acid; 1,1-Dimethylethylenediamine; 1,2-Dimethylethylenediamine; Dimethylglyoxime; DIOP; Diphenylethylenediamine; 1,5-Dithiacyclooctane; Domoic acid; DOTA; DOTA-TATE; DTPMP; EDDHA; EDDS; EDTA; EDTMP; EGTA; 1,2-Ethanedithiol; Ethylenediamine; Ethylenediaminediacetic acid; Ethylenediaminetetraacetic acid; Etidronic acid; Fluo-4; Fura-2; Gallic acid; Gluconic acid; Glutamic acid; Glyoxal-bis(mesitylimine); Glyphosate; Hexafluoroacetylacetone; Homocitric acid; Iminodiacetic acid; Indo-1; Isosaccharinic acid; Kainic acid; Ligand; Malic acid; Metal acetylacetonates; Metal dithiolene complex; Metallacrown; Nitrilotriacetic acid; Oxalic acid; Oxime; Pendetide; Penicillamine; Pentetic acid; Phanephos; Phenanthroline; O-Phenylenediamine; Phosphonate; Phthalocyanine; Phytochelatin; Picolinic acid; Polyaspartic acid; Porphine; Porphyrin; 3-Pyridylnicotinamide; 4-Pyridylnicotinamide; Pyrogallol; Salicylic acid; Sarcophagine; Sodium citrate; Sodium diethyldithiocarbamate; Sodium polyaspartate; Terpyridine; Tetramethylethylenediamine; Tetraphenylporphyrin; Thenoyltrifluoroacetone; Thioglycolic acid; TPEN; 1,4,7-Triazacyclononane; Tributyl phosphate; Tridentate; Triethylenetetramine; Triphos; Trisodium citrate; 1,4,7-Trithiacyclononane; and TTFA and derivatives thereof.

In some embodiments, the metal ion is $Ca^{2+}$. Optionally, the chelator or the derivatized chelator for $Ca^{2+}$ is selected from the group consisting of ethylene glycol-bis(R-aminoethyl ether)-N,N,N',N'-tetraacetic acid (EGTA); ethylene diamine tetra acetic acid (EDTA); N-(2-Hydroxyethyl)ethylenediamine-N, N', N'-triacetic acid Trisodium salt (HEDTA); Nitrilotriacetic acid (NTA); BAPTA; 5,5'-dimethyl BAPTA (such as tetrapotassium salt); DMNP-EDTA; INDO 1 (such as pentapotassium salt); FURA-2 (such as pentapotassium salt); FURA 2/AM; MAPTAM; FLUO 3 (such as pentaammonium salt); Tetraacetoxymethyl Bis(2-aminoethyl) Ether N,N,N',N'-Tetraacetic Acid; 2-{(carboxymethyl) 2-trimethylamino ethyl amino}acetic acid and salts of such agents, as well as free acids, derivatives and combinations thereof. Preferably, the chelator or the derivatized chelator for $Ca^{2+}$ is EGTA or a derivative thereof.

In some embodiments, the metal ion is $Fe^{2+}$ or $Fe^{3+}$. Optionally, the chelator or derivatized chelator for $Fe^{2+}$ or $Fe^{3+}$ is selected from the group consisting of deferasirox; deferiprone; deferoxamine; desferrioxamine; desferrithiocin [2-(3-hydroxypyridin-2-yl)-4-methyl-4,5-dihyrothiazole-4-carboxylic acid; clioquinol; O-trensox (Tris-N-(2-aminoethyl-[8-hydroxyquinoline-5-sulfonato-7-carboxamido] amine); tachpyr (N,N',N"-tris(2-pyridylmethyl)-cis,cis-1,3,5-triamino-cyclohexane); dexrazoxane; triapine (3-aminopyridine-2-carboxaldehyde thiosemicarbazone); pyridoxal isonicotinoyl hydrazone; di-2-pyridylketone thiosemicarbazone series; flavan-3-ol; curcumin; apocynin; kolaviron; floranol; baicalein; baicalin; *Ligusticum wallichi* Francha (ligustrazine); quercetin; epigallocatechin gallate; theaflavin; phytic acid; genistein (5,7,4'-tri-hydroxyisoflavone); EDTA; NTA; HBED, o-Phenanthroline monohydrate; Pyridoxal Isonicotinoyl Hydrazone, 2,2prime-Dipyridyl, (S) 1 (p Bromoacetamidobenzyl) ethylenediaminetetraacetic Acid, (S) 1 (4 Aminoxyacetamidobenzyl)ethylenediaminetetraacetic Acid; Lipoic Acid and salts of such agents, as well as the free acids, derivatives thereof and combinations thereof.

In some embodiments, the metal ion is $Mg^{2+}$. Optionally, the chelator or the derivatized chelator for $Mg^{2+}$ is selected from the group consisting of EDTA, EGTA, HEDTA, NTA and salts of such agents, as well as the free acids, derivatives thereof and combinations thereof.

In some embodiments, the metal ion is $Mn^{2+}$. Optionally, the chelator or the derivatized chelator for $Mn^{2+}$ is selected from the group consisting of EDTA; EGTA; HEDTA; NTA; triethylenetetramine-N,N,N',N",N''',N'''-hexaacetic acid (TTHA); para-aminosalicylic acid (PAS), 1,2-cyclohexylenedinitrilotetraacetic acid (CDTA), nitrilotriacetic acid (NAS), diethylenetriaminepentaacetic acid (DTPA); DPTA-OH; HBED; and salts of such agents, as well as the free acids, derivatives thereof and combinations thereof.

In some embodiments, the metal ion is $Cu^{2+}$ or $Cu^{3+}$. Optionally, the chelator or the derivatized chelator for $Cu^{2+}$ or $Cu^{3+}$ is selected from the group consisting of EDTA; NTA; D-Penicillamine (DPA); Tetraethylenetetraamine (TETA); clioquinol; glutamic acid; lipoic acid; and salts of such agents, as well as the free acids, derivatives thereof and combinations thereof.

In some embodiments, the metal ion is $Zn^{2+}$. Optionally, the chelator or the derivatized chelator for $Zn^{2+}$ is selected from the group consisting of ADAMTS-5 Inhibitor; N,N,N',N'-tetrakis(2-pyridinylmethyl)-1,2-ethanediamine (TPEN); EDPA; 1,2-bis(o-aminophenoxy)ethane-N,N,N',N'-tetraacetic acid (BAPTA); CaEDTA; EDTA; EGTA; Tricine; ZX1; 4-{[2-(bis-pyridin-2-ylmethylamino)ethylamino]methyl}phenyl)methanesulfonic acid (DPESA); [4-({[2-(bis-pyridin-2-ylmethylamino)ethyl]pyridin-2-ylmethylamino}-methyl)phenyl]methanesulfonic acid (TPESA); and derivatives thereof.

In some embodiments, the metal ion is $Ni^{2+}$. Optionally, the chelator or the derivatized chelator for $Ni^{2+}$ is selected from the group consisting of citrate, malate, histidine, EDTA, sodium diethyldithiocarbamate (Dithiocarb), dimethyldithiocarbamate, diisopropyl, morpholine-I-dithiocarbamate, N,N'-ethylene-bis-dithiocarbamate, 2-2(oxo-1-imidazo-lidyl) ethyldithiocarbamate, dithiocarbamate, tetraethylthiuram (Antabuse), d-penicillamine, dimercaprol (BAL), N-methyl formamide, 8-Hydroxyquinoline-Cyclodextrin Conjugate, glutamic acid and salts of such agents, as well as the free acids, derivatives thereof and combinations thereof. In some embodiments the chelator or derivatized chelator for $Ni^{2+}$ is a nickel binding protein. See, e.g., Sudan R J J, et al. (2015) Ab Initio Coordination Chemistry for Nickel Chelation Motifs. PLoS ONE 10(5): e0126787. doi: 10.1371/journal.pone.0126787, incorporated by reference herein in its entirety.

In some embodiments, the metal ion is $Co^{2+}$. Optionally, the chelator or the derivatized chelator for $Co^{2+}$ is selected from the group consisting of L-cysteine; L-methionine; N-acetyl-cysteine; EDTA; sodium 2,3-dimercaptopropane sulfonate (DMPS); diethylenetriaminepentaacetic acid (DTPA); 2,3-dimercaptosuccinic acid (DMSA); dimercaprol; 8-Hydroxyquinoline-Cyclodextrin Conjugate; glutamic acid; deferasirox; desferrioxamine; deferiprone; and salts of such agents, as well as the free acids, derivatives thereof and combinations thereof.

In some embodiments, the metal ion is a heavy metal ion. Optionally, the heavy metal ion is selected from the group consisting of $As^{+3}$, $Hg^{+2}$, $Sb^{+3}$, and $Au^+$. In some embodiments, the chelator or the derivatized chelator for the heavy metal ion is selected from the group consisting of Dimercaprol (2,3-dimercapto-1-propanol); Sodium 2,3 dimercaptopropanesulfonate monohydrate; 2,3-Dimercapto-1-propanesulfonic acid sodium salt; Dimercaptosuccinic acid; Penicillamine; Lipoic Acid; and salts of such agents, as well as the free acids, derivatives thereof and combinations thereof. In some embodiments, the chelator or derivatized chelator for $Au^+$ comprises an SH group. Optionally, the chelator or derivatized chelator for $Hg^{2+}$ comprises an SH group.

In some embodiments, the field-effect transistor of the sensor or method of the disclosure is any of the field-effect transistors disclosed herein.

In some embodiments, the marker detected by the sensor or the method is a biomarker, an environmental marker, an allergen, or a microorganism. In some embodiments, the sample is an environmental sample, a food sample, or a sample obtained from a subject.

In some embodiments, the device further comprises means for removing the marker not bound to the antibody. In some embodiments, the device comprises means for washing or filtering the antibody-bound marker.

EXAMPLES

The following examples are offered for illustrative purposes only and do not limit the scope of the present disclosure or paragraphs in any way. Indeed, various modifications of the disclosure in addition to those shown and described herein will become apparent to those skilled in the art from the foregoing description and fall within the scope of the paragraphs.

Example 1: Synthesis of the Mono-Thiolated EGTA (EGTA-SH) and Functionalization of the FET Substrate In order to attach EGTA to the surface of the substrate 5 (FIG. 2A), EGTA was derivatized to incorporate one thiol group (EGTA-SH). The surface of the substrate was then functionalized with phenylmaleimide. The thiol derivatized EGTA (EGTA-SH) was then cross-linked to the maleimide group on the surface of the substrate. These steps were accomplished as described below.

Method 1

Potassium thioacetate was diluted and added dropwise into a solution of 1,4-diioidobutane to afford the corresponding thioester. The thioester was then diluted and added slowly to a dilute solution of $K_4$EGTA, resulting in the formation of the mono-functionalized thioester-$K_3$EGTA. Thioester-$K_3$EGTA was then reacted with KOH followed by neutralization with HCl to afford EGTA-SH.

Method 2

2-aminoethane-1-thiol was added to a solution of protected EGTA. The resulting thiol was deprotected to afford the final product. The reaction required dissolving in DMF at room temperature for 4 hrs. The structure was confirmed via NMR.

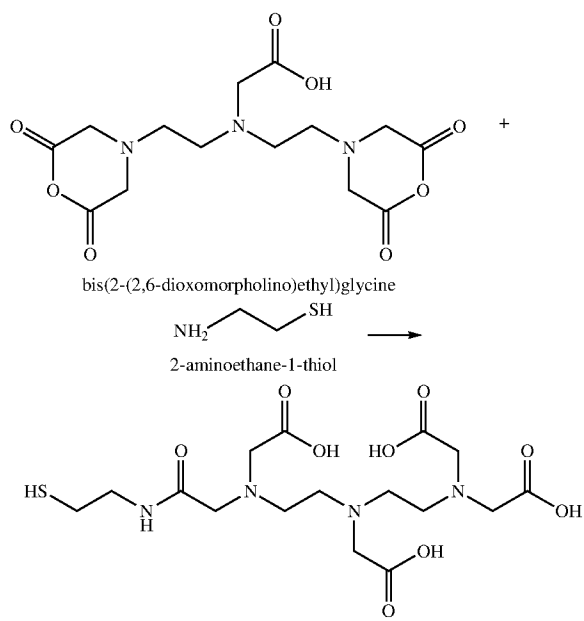

Method 3

Another method which could be used to form EGTA thioester involves the reaction of EGTA with 1-pyrenebutyric acid to form a thioester. The EGTA thioester is adsorbed onto a Platinum or a carbon nanotube surface, which is interposed between the source contact and the drain contact of a FET.

Synthesis of (p-Diazophenyl)Maleimide Tosylate

N-(4-aminophenyl)maleimide was synthesized according to one of the following two methods:
  (a) conversion of 1,4-phenylenediamine to (E)-4-((4-aminophenyl)amino)-4-oxobut-2-enoic acid upon treatment with maleic anhydride, followed by cyclisation to N-(4-aminophenyl)maleimide using $P_2O_5$ (see for example, *Histochemical Journal*, 5, 1973, 413-423); or
  (b) reduction of (p-nitrophenyl)maleimide upon treatment with sodium dithionite (see for example, *Org. Lett.*, 10, No. 18, 2008, 3961-3964).

Diazotization of N-(4-aminophenyl)maleimide was subsequently carried out using a polymer-supported diazotization agent, i.e., a modified resin containing nitrite ions (Resin-$NO_2$) as described in Fillimonov, V. D., et al. (*Org. Lett.*, 10, No. 18, 2008, 3961-3964).

The diazonium salt is covalently bonded to Platinum and to a carbon nanotube surface by applying a voltage.

Once the surface of the substrate is functionalized with phenylmaleimide, the phenylmaleimide is crosslinked with EGTA-SH, thus attaching EGTA to the substrate surface.

Upon contacting a composition comprising $Ca^{+2}$ ions with a sensor comprising EGTA-coated Field Effect Transistors, the detection of the $Ca^{+2}$ ions was improved compared to sensors that do not comprise EGTA coating.

Example 2: SH-EGTA Chelation of Divalent and Trivalent Ions

The chelation behavior of EGTA-thioacetate to $Ca^{2+}$, $Cr^{3+}$, $Co^{2+}$ and $Cu^{2+}$ was determined by measuring the absorbance at different wavelengths and comparing with protonated EGTA. 2 mM samples were used for the determination.

As shown on FIGS. 8A-8C for $Cr^{3+}$, $Co^{2+}$ and $Cu^{2+}$, all sodium-based EGTA analogues had an 18-19 nm shift in the $\lambda_{max}$ comparing to the protonated EGTA, which does not show change in $\lambda_{max}$. Additionally, the EGTA-thioacetate ligands had a significant increase in absorbance compared to the sodium-based EGTA analogues and the protonated EGTA. This could be confirmed for $Ca^{2+}$, $Cr^{3+}$, $Co^{2+}$ and $Cu^{2+}$.

The chelation behavior of the thioacetate-EGTA to Cr3+, Co2+, and Cu2+ suggests that the SH-EGTA is chelating these ions.

The calcium binding affinity was determined by using the Bers method (Bers DM. Am J Physiol. 1982; 242(5):C404-8):

$$\frac{[Ca^{2+}EGTA]}{[Ca^{2+}]} = -K_{app}^{bound} + [EGTA]_{total}K_{app}$$

Briefly, free $Ca^{2+}$ in Ca-EGTA solutions was measured with a Ca electrode, bound Ca was calculated, and Scatchard and double-reciprocal plots were resolved for the total EGTA and the apparent Ca-EGTA association constant ($K_{app}$) in the solutions used. The free $Ca^{2+}$ was then recalculated using the determined parameters, giving a more accurate knowledge of the free $Ca^{2+}$ in these solutions and providing an accurate calibration curve for the Ca electrode. This method allows determination of free $Ca^{2+}$, $K_{app}$, and total EGTA in the actual solutions used regardless of pH, temperature, or ionic strength.

In order to calculate the calcium binding affinity of EGTA, the steps below were followed:
  (a) The calcium potential was measured in four calibration solutions (1-4 mmol/L). The pH was adjusted to pH 7.2 by adding KOH or HCL.
  (b) The potential of background solution was measured with no added EGTA or $Ca^{2+}$ to check for calcium contamination.
  (c) The calibration curve of potential (mV) vs. pCa=−log $[Ca^{2+}]$ was plotted and fit a line.
  (d) The potential for calcium containing solutions was measured, where the free calcium was calculated from:

[Ca2+](free)=[Ca2+](total)[Ca2+EGTA]/([Ca2+EGTA]+[EGTA])

(e) [Ca2+](free) and the ratio [Ca2+EGTA]/[Ca2+] (bound/free) were calculated.
  (f) Kapp was computed and also Kd (Kd=1/Kapp)

Example 3: GaN/AlGaN FET Device

The transistor comprises a source (2) and a drain (3) deposited onto the substrate (5). See FIG. 1. For the top surface passivation of the source and the drain, two options, 100 nm $Si_3N_4$ and Benzocyclobutene (non-polar film) were evaluated. The two options were assessed for FET discharge damage in the source-drain and for linear dependence of the current versus the voltage at different input voltages. The best results were obtained using $Si_3N_4$ or $Si_3N_4/SiO_2$. FIG. 1 and FIG. 3 show the layout of the FET device used in the present application.

The substrate (5), in this example, comprised the following layers, from bottom to top: a SiC layer (34), a AlN layer (33), a carbon doped GaN layer (32), a UID GaN layer (31) and a top layer of AlGaN (30). A gate metallization of Ti/Au or Ti/Pt (23) was deposited over the ohmic metal (22) and was encapsulated by a layer of $SiN_3$ (24). See FIG. 1 and FIG. 3.

The FET geometry designs was as follows (see FIG. 5):
Constants in the Geometries
  Device width: 50 μm
  Gate Electrode Length: 100 μm
  Active Region opening width: 50 μm
  Source to Drain spacing: 30 μm
Variables:
  Gate Electrode Width: 60 and 120 μm
  Active Region opening Length: 10 and 5 μm
  Gate Separation: 65, 265, 465 μm

Example 4: Detection of an Analyte Using a FET Device

The amplification approach of the analyte is based on the rapid release of calcium ions ($Ca^{2+}$) near the sensor-liquid-interface. The capture antibody and the chelator (EGTA) were conjugated to the substrate surface. See FIGS. 2A-2D.

The detection antibody, linked to liposomes containing the calcium ions, selectively recognizes the target analyte. The conjugate liposomes-antibody-analyte were put into contact with the capture antibody conjugated to the substrate surface.

A wash step was performed to remove the free liposomes conjugated to detection antibodies, not specifically bound to the analyte.

A detergent (a non-ionic detergent, Triton X-100) was used to destabilize and disrupt the phospholipid bilayers of liposomes, so that the release of the calcium ions occurred.

To bring $Ca^{2+}$ ions near the surface of the channel or gate, EGTA was conjugated to the substrate surface and bound $Ca^{2+}$ ions near the FET gate. See FIGS. 2A-2D.

If the analyte has bound to the detection and capture antibodies and calcium ions have been released upon disruption of the liposomes, this results in a detectable voltage shift associated with the change in current across the transistor due to the binding of $Ca^{2+}$ at the substrate surface, changing the transistor's electronic characteristics. The change in current was measured using cyclic voltammetry, specifically, a potentiostat. In particular, the measurements confirmed a linear drain current dependence for the gate bias based on differing input voltage (−5V, −2V, 0V, 1V, 2V, 3V and 4V). See FIGS. 7A and 7B, where the graphs show IL (drain current) as a function of $V_d$ (drain voltage) of the measured dry $I_d$-$V_d$ curves for the present FET transistor. As the gate bias is increased, the slopes of the linear portion of the I-V characteristics in FIG. 7A gradually increased as a result of the increasing conductivity of the channel.

The invention claimed is:

1. A method for the detection of a target marker in a solution including charged ions and unrelated ions comprising:

providing a liposome in solution containing metal ions, the liposome including a detection antibody configured to bind a target marker;

providing a field-effect transistor with a source-drain channel comprising a surface functionalized with both a capture antibody to selectively bind to the target marker and a metal ion chelator or metal ion derivatized chelator;

selectively binding the target marker to the detection antibody included with the liposome;

selectively binding the target marker to the capture antibody to dispose the target marker and bound liposome to the source-drain channel of the field-effect transistor;

releasing the metal ions from the liposome;

selectively binding the metal ion chelator or metal ion derivatized chelator disposed on the functionalized surface of the source-drain channel with the metal ions released from the liposome; and causing a change in current in the field-effect transistor as a result of the selective binding of the metal ion chelator or metal ion derivatized chelator with the metal ions released from the liposome without interference of the detection of the metal ions by screening oppositely charged ions and unrelated ions in the solution; and wherein the change in current is indicative of detection of the target marker.

2. The method of claim 1, wherein the field-effect transistor comprises a substrate comprising gallium nitride.

3. The method of claim 1, wherein the field-effect transistor further comprises a carbon nanotube.

4. The method according to claim 3, wherein the carbon nanotube is at least partially interposed between the source and the drain.

5. The method of claim 1, wherein the metal ion is $Ca^{2+}$.

6. The method of claim 1, wherein the metal ion is $Fe^{2+}$ or $Fe^{3+}$.

7. The method according to claim 6, wherein the chelator or derivatized chelator is selected from the group consisting of deferasirox; deferiprone; deferoxamine; desferrioxamine; desferrithiocin[2-(3-hydroxypyridin-2-yl)-4-methyl-4,5-dihyrothiazole-4-carboxylic acid; clioquinol; O-trensox (Tris-N-(2-aminoethyl-[8-hydroxyquinoline-5-sulfonato-7-carboxamido] amine; tachpyr (N,N',N''-tris(2-pyridylmethyl)-cis,cis-1,3,5-triamino-cyclohexane); dexrazoxane; triapine (3-aminopyridine-2-carboxaldehyde thiosemicarbazone); pyridoxal isonicotinoyl hydrazone; di-2-pyridylketone thiosemicarbazone series; flavan-3-ol; curcumin; apocynin; kolaviron; floranol; baicalein; baicalin; *Ligusticum wallichi* Francha (ligustrazine); quercetin; epigallocatechin gallate; theaflavin; phytic acid; genistein (5,7,4'-tri-hydroxy-isoflavone); EDTA; NTA; HBED, o-Phenanthroline monohydrate; Pyridoxal Isonicotinoyl Hydrazone, 2,2prime-Dipyridyl, (S)-1-(p-Bromoacetamidobenzyl)ethylenediaminetetraacetic Acid, (S)-1-(4-Aminoxyacetamidobenzyl) ethylenediaminetetraacetic Acid; and derivatives thereof.

8. The method of claim 1, wherein the metal ion is $Mg^{2+}$.

9. The method according to claim 8, wherein the chelator or the derivatized chelator is selected from the group consisting of EDTA, EGTA, HEDTA, NTA and derivatives thereof.

10. The method of claim 1, wherein the metal ion is $Mn^{2+}$.

11. The method according to claim 10, wherein the chelator or the derivatized chelator is selected from the group consisting of EDTA; EGTA; HEDTA; NTA; triethyl-enetetramine-N,N,N',N'',N''',N''''-hexaacetic acid (TTHA);

diethylenetriaminepentaacetic acid (DTPA); DPTA; DPTA-OH; HBED; and derivatives thereof.

12. The method of claim 1, wherein the metal ion is $Cu^{2+}$ or $Cu^{3+}$.

13. The method according to claim 12, wherein the chelator or the derivatized chelator is selected from the group consisting of EDTA; NTA; D-Penicillamine (DPA); Tetraethylenetetraamine (TETA); clioquinol and derivatives thereof.

14. W The method of claim 1, wherein the metal ion is $Zn^{2+}$.

15. The method according to claim 14, wherein the chelator or the derivatized chelator is selected from the group consisting of ADAMTS-5 Inhibitor; N,N,N',N'-tetrakis(2-pyridinylmethyl)-1,2-ethanediamine (TPEN); EDPA; 1,2-bis(o-aminophenoxy)ethane-N,N,N',N'-tetraacetic acid (BAPTA); CaEDTA; EDTA; EGTA; Tricine; ZX1; 4-{[2-(bis-pyridin-2-ylmethylamino)ethylamino]methyl}phenyl) methanesulfonic acid (DPESA); [4-({[2-(bis-pyridin-2-ylmethylamino)ethyl]pyridin-2-ylmethylamino}-methyl) phenyl]methanesulfonic acid (TPESA); and derivatives thereof.

16. The method of claim 1, wherein the metal ion is $K^+$.

17. The method according to claim 16, wherein the chelator or the derivatized chelator is selected from the group consisting of calcium polystyrene sulfonate; sodium polystyrene sulfonate; patiromer; sodium zirconium cyclosilicilate; D-tartrate monobasic; and derivatives thereof.

18. The method of claim 1, wherein the metal ion is a heavy metal ion.

19. The method according to claim 18, wherein the heavy metal ion is selected from the group consisting of $As^{+3}$, $Hg^{+2}$, $Sb^{+3}$, and $Au^+$.

20. The method according to claim 19, wherein the chelator or the derivatized chelator is selected from the group consisting of Dimercaprol (2,3-dimercapto-1-propanol); Sodium 2,3-dimercaptopropanesulfonate monohydrate; 2,3-Dimercapto-1-propanesulfonic acid sodium salt; and derivatives thereof.

21. The method of claim 1, wherein the target marker is a biomarker, an environmental marker, an allergen, or a microorganism.

22. The method of claim 1, wherein the metal ions are is released from the liposome by contacting the liposome with a detergent.

* * * * *